United States Patent
Manin et al.

(10) Patent No.: US 12,052,969 B2
(45) Date of Patent: Aug. 6, 2024

(54) QUALITY AND PERMANENCE OF GREEN COLOR OF PEPPERS AT MATURITY AND OVER-MATURITY

(71) Applicant: VILMORIN & CIE, Paris (FR)

(72) Inventors: Sylvie Manin, Ledenon (FR); Alain Chiron, Ledenon (FR)

(73) Assignee: VILMORIN & CIE, Paris (FR)

( * ) Notice: Subject to any disclaimer, the term of this patent is extended or adjusted under 35 U.S.C. 154(b) by 91 days.

(21) Appl. No.: 17/621,566

(22) PCT Filed: Jun. 19, 2020

(86) PCT No.: PCT/EP2020/067241
§ 371 (c)(1),
(2) Date: Dec. 21, 2021

(87) PCT Pub. No.: WO2020/254655
PCT Pub. Date: Dec. 24, 2020

(65) Prior Publication Data
US 2022/0354079 A1    Nov. 10, 2022

(30) Foreign Application Priority Data

Jun. 21, 2019  (WO) ................. PCT/IB2019/000677

(51) Int. Cl.
| | |
|---|---|
| A01H 5/08 | (2018.01) |
| A01H 1/00 | (2006.01) |
| A01H 5/00 | (2018.01) |
| A01H 6/82 | (2018.01) |

(52) U.S. Cl.
CPC ............ *A01H 6/822* (2018.05); *A01H 1/00* (2013.01); *A01H 5/00* (2013.01); *A01H 5/08* (2013.01); *C12Q 2600/13* (2013.01)

(58) Field of Classification Search
None
See application file for complete search history.

(56) References Cited

U.S. PATENT DOCUMENTS

2006/0195921 A1* 8/2006 Van Der Heiden ...... A01H 1/04
800/278
2012/0278944 A1  11/2012 Wang et al.

FOREIGN PATENT DOCUMENTS

| CA | 2 902 250 A1 | 2/2017 |
| CN | 109207622 A | 1/2019 |
| KR | 10-1983907 B1 | 5/2019 |
| WO | 2004/089067 A1 | 10/2004 |
| WO | 2014/204815 A1 | 12/2014 |

OTHER PUBLICATIONS

Borovsky et al., "Chlorophyll breakdown during pepper fruit ripening in the chlorophyll retainer mutation is impaired at the homolog of the senescence-inducible stay-green gene", Theor Appl Gent, 2008, pp. 235-240.
Cheng et al., "Variation in leaf color and combine effect of pigments on physiology and resistance to whitefly of pepper (*Capsicum annuum* L.)", Scientia Horticulturae, Nov. 9, 2017, pp. 215-225, vol. 229.
Comai et al., "Efficient discovery of DNA polymorphisms in natural populations by Ecotilling", The Plant Journal, 2004, pp. 778-786.
De Jonge et al., "A seed treatment to prevent shoot apical meristem arrest in *Brassica oleracea*", Scientia Horticulturae, 2018, pp. 76-80.
Farré et al., "Travel advice on the road to carotenoids in plants", Plant Science, 2010, pp. 28-48, vol. 179.
Gao et al., "DNA-guided genome editing using the Natronobacterium gregoryi Argonaute", Nature Biotechnology, Jul. 2016, pp. 768-776, vol. 34.
Hurtado-Hernandez et al., "Inheritance of mature fruit color in *Capsicum annuum* L.", The Journal of Heredity, 1985, pp. 211-213, vol. 76.
Kang et al., "Optimization of Tilling system based on capillary electrophoresis for targeted selection of pepper gene mutants", Horticulture, Environment, and Biotechnology, May 29, 2018, 14 pages.
Kim et al., "A New Nonsense Mutation in Capsanthin/Capsorubin Synthase Controlling Orange Pepper Fruit", Horticultural Science and Technology, 2017, pp. 599-607, vol. 35, No. 5.
Lefebvre et al., "The capsanthin-capsorubin synthase gene: a candidate gene for the y locus controlling the red fruit colour in pepper", Plant Molecular Biology, 1998, pp. 785-789, vol. 36.
O. R. Kim et al., "A Splicing Mutation in the Gene Encoding Phytoene Synthase Causes Orange Coloration in Habanero Pepper Fruits", Molecules and Cells, Dec. 31, 2010, pp. 569-574, vol. 30.
Cheng Qin et al., "Whole-genome sequencing of cultivated and wild peppers provides insights into Capsicum domestication and specialization", Proceedings of the National Academy of Sciences, Apr. 8, 2014, pp. 5135-5140, vol. 111 No. 14.
T. A. Thorup et al., "Candidate gene analysis of organ pigmentation loci in the Solanaceae", Proceedings of the National Academy of Sciences, Oct. 10, 2000, pp. 11192-11197, vol. 97 No. 21.

(Continued)

*Primary Examiner* — Phuong T Bui
(74) *Attorney, Agent, or Firm* — Oliff PLC

(57) ABSTRACT

*Capsicum* plants produce fruits which are and remain green at maturity and/or over-maturity, and not olive green like existing evergreen varieties. The plants homozygously include in their genome a mutant allele of the cl gene encoding the *Capsicum* stay-green (CaSGR) protein and a mutant allele of the wt gene encoding the phytoene synthase (PSY) protein. Further, parts and cells of the plants, in particular pepper fruits are and remain green at maturity and/or over-maturity. Moreover, methods for producing the *Capsicum* plants and methods identify, detect and/or select the plants.

9 Claims, 10 Drawing Sheets
Specification includes a Sequence Listing.

(56) References Cited

OTHER PUBLICATIONS

B. J. Till et al., "A protocol for Tilling and Ecotilling in plants and animals", Nature Protocols, 2006, pp. 2465-2477, vol. 1 No. 5.

J.W. van Ooijen, "Software for the calculation of genetic linkage maps in experimental populations", JoinMap 4, Kyazma B.V., Wegeningen, Netherlands, Jul. 2004, 63 pages.

J.W. van Ooijen, "Software for the mapping of quantitative trait loci in experimental populations", MapQTL 5, Kyazma B.V., Wageningen, Netherlands, Feb. 2004, 63 pages.

Wetzstein et al., "Morphological Evaluation of Apical Meristem Decline in Greenhouse-grown Tomato Transplants and the Effect of Mineral Nutrition on Its Occurrence", Journal of the American Society for Horticultural Science, 2002, pp. 635-638, vol. 127 No. 4.

Wu et al., "A COSII genetic map of the pepper genome provides a detailed picture of synteny with tomato and new insights into recent chromosome evolution in genus *Capsicum*", Theor Appl Genet, 2009, pp. 1279-1293.

Aug. 13, 2020 International Search Report issued in International Patent Application No. PCT/EP2020/067241.

Aug. 13, 2020 Written Opinion issued in International Patent Application No. PCT/EP2020/067241.

\* cited by examiner

A.

B.

A.

B.

A.

B.

A.

B.

A.

B.

SEQUENCE LISTING

```
<160> NUMBER OF SEQ ID NOS: 13

<210> SEQ ID NO 1
<211> LENGTH: 995
<212> TYPE: DNA
<213> ORGANISM: Capsicum annuum

<400> SEQUENCE: 1
cacaactcct ctttaagttt ctactcattc tctttgccaa ctttgatcaa aaacaccttta    60 taataaattg atcaagattc aaggagtttt gggtacccaa tttcttgatg aaatggggac   120
tttgactgct tctctagtag ctccatctaa gctcaaccct gaaaagcata gctctctttt   180
tgtatacaaa actagaagaa agtcccacaa gaatcaatcc atagtccctg tggcaaggct   240
atttggacca gctatatttg aagcatcaaa gttgaaggta cttttcttgg gagttgatga   300
gaaaaagcac ccaggaaagt tgccaagaac atatacactg actcatagtg atattacttc   360
taaactcact ttggcaatct ctcaaaccat caataactct cagttgcaag gttggtataa   420
tagacttcaa agggatgaag tggttgcaga atggaagaaa gttaaaggga agatgtcact   480
ccatgtacat tgccacatta gtggaggcca ttttatgtta gacttatttg ctagactcag   540
atactatatc ttctgcaaag aactccctgt ggttctgaag gcttttgttc atggagatga   600
gaatttacta aagaattatc cagagttgca acaagcttta gtttgggtat attttcactc   660
aaacattcaa gaattcaaca aagtagaatg ttggggccca ctcaaagatg cagcctcccc   720
ctcatcaagt ggggtaggtg ggggtatgaa tacaagtttt acaagcaata gcaacatcaa   780
gtggaattta ccaaagcctt gtgaagagac ttgtacatgt tgctttcccc caatgagtgt   840
tatcccttgg ccttctacta ctaatgtgga aaatgggacc atacaacaag gcttgcaaga   900
gcagcaaagc tgaaaaaaga cagtaattct gttgctttat tatgtgattt gatgtaatta   960
attaattaat taattatcat cattataggg tttgt                               995

<210> SEQ ID NO 2
<211> LENGTH: 266
<212> TYPE: PRT
<213> ORGANISM: Capsicum annuum

<400> SEQUENCE: 2

Met Gly Thr Leu Thr Ala Ser Leu Val Ala Pro Ser Lys Leu Asn Pro
1               5                   10                  15

Glu Lys His Ser Ser Leu Phe Val Tyr Lys Thr Arg Arg Lys Ser His
            20                  25                  30
```

```
Lys Asn Gln Ser Ile Val Pro Val Ala Arg Leu Phe Gly Pro Ala Ile
             35                  40                  45

Phe Glu Ala Ser Lys Leu Lys Val Leu Phe Leu Gly Val Asp Glu Lys
 50                  55                  60

Lys His Pro Gly Lys Leu Pro Arg Thr Tyr Thr Leu Thr His Ser Asp
 65                  70                  75                  80

Ile Thr Ser Lys Leu Thr Leu Ala Ile Ser Gln Thr Ile Asn Asn Ser
                 85                  90                  95

Gln Leu Gln Gly Trp Tyr Asn Arg Leu Gln Arg Asp Glu Val Val Ala
            100                 105                 110

Glu Trp Lys Lys Val Lys Gly Lys Met Ser Leu His Val His Cys His
            115                 120                 125

Ile Ser Gly Gly His Phe Met Leu Asp Leu Phe Ala Arg Leu Arg Tyr
130                 135                 140

Tyr Ile Phe Cys Lys Glu Leu Pro Val Val Leu Lys Ala Phe Val His
145                 150                 155                 160

Gly Asp Glu Asn Leu Leu Lys Asn Tyr Pro Glu Leu Gln Gln Ala Leu
                165                 170                 175

Val Trp Val Tyr Phe His Ser Asn Ile Gln Glu Phe Asn Lys Val Glu
            180                 185                 190

Cys Trp Gly Pro Leu Lys Asp Ala Ala Ser Pro Ser Ser Ser Gly Val
            195                 200                 205

Gly Gly Gly Met Asn Thr Ser Phe Thr Ser Asn Ser Asn Ile Lys Trp
            210                 215                 220

Asn Leu Pro Lys Pro Cys Glu Glu Thr Cys Thr Cys Cys Phe Pro Pro
225                 230                 235                 240

Met Ser Val Ile Pro Trp Pro Ser Thr Thr Asn Val Glu Asn Gly Thr
                245                 250                 255

Ile Gln Gln Gly Leu Gln Glu Gln Gln Ser
            260                 265

<210> SEQ ID NO 3
<211> LENGTH: 2040
<212> TYPE: DNA
<213> ORGANISM: Capsicum annuum

<400> SEQUENCE: 3
tacaaagaaa aatgaaaaaa aattacgtaa tataataatt tttaaaaatt aaataatgaa      60
tgctataaat agaccaaatt atgtggagca ataaagagg agaaaaacca acaaactact      120
tgtaattctt gaagaataca aagcagacat tgttgaaaag tggccatttt tgcaagaagc      180
caagaaatag gttatttctt gtttgatag tggaagtata ctctagtggg aatctactag      240
gagttactta ttttctataa agaagacaaa aaccttggag ttgctttaga caaccaaggt      300
ttttcttgtt cagaatgtct gttgccttgt tatgggttgt ttctccttgt gacgtctcaa      360
acgggacagg attcttggta tccgttcgtg agggaaaccg gattttttgat tcgtcgggc       420 gtaggaattt ggcgtgcaat gagagaatca agagaggagg tggaaaacaa aggtggagtt      480
ttggttcttg cttgggagga gcacaaactg gaagtggacg gaaattttct gtacgttctg      540
ctatcgtggc tactccggct ggagaaatga cgatgtcatc agaacggatg gtatatgatg      600
tggttttgag gcaggcagcc ttggtgaaga acagctgag atcgaccgat gagttagatg       660
tgaagaagga tatacctatt ccggggactt tgggcttgtt gagtgaagca tatgataggt      720
gtagtgaagt atgtgcagag tacgcaaaga cgttttactt aggaacgatg ctaatgactc      780
```

```
cggagagaag aaaggctatc tgggcaatat acgtatggtg caggagaaca gacgaacttg    840
ttgatggtcc gaatgcatca cacattactc cggcggcctt agataggtgg aagacaggc    900 tagaagatgt tttcagtgga cggccatttg acatgctcga tgctgctttg tccgacacag    960
tttccaaatt tccagttgat attcagccat tcagagatat gattgaagga atgcgtatgg   1020
acttgaggaa gtcaagatac agaaactttg acgaactata cctatattgt tattacgttg   1080
ctggtacggt tgggttgatg agtgttccaa ttatgggcat cgcacctgaa tcaaaggcaa   1140
caacggagag cgtatataat gctgctttgg ctttggggat cgcaaatcag ctgaccaaca   1200
tacttagaga tgttggagaa gatgccagaa gaggaagagt ctatttgcct caagatgaat   1260
tagcacaggc aggtctatcc gacgaagaca tatttgctgg aagagtgacc gataaatgga   1320
gaatcttcat gaagaaacaa attcagaggg caagaaagtt cttttgacgag gcagagaaag   1380 gagtgaccga attgagcgca gctagtagat ggcctgtgtt ggcatctctg ctgttgtacc   1440
gcaggatact ggacgagatc gaagccaatg actacaacaa cttcacaaag agagcttatg   1500
tgagcaaacc aaagaagttg attgcattac ctattgcata tgcaaaatct cttgtgcctt   1560
ctacaagaac atgaaatcag gattttatat aaatcaaggc caatgaagcc aatatacatt   1620
tagaagaaaa aaaacaagtg tttataaagt agaattattg aaggggaggc ttggagtaac   1680
tggtaaagtt gttgtcatgt gactgggaag tcacgggttc aagccttgga aacagcctct   1740
ggcagaaatg caaggtaagg ttgcgtacaa tataccgtta aggtggggtc cttcccagta   1800
caccgcgcat agcgatagat ttagtgcacc gggtcgcctt ttttctaaag tagaataatt   1860
gttgtattca tgtcaatgta tatcatcaaa attaggtggt agtaaaatcc aatgtaacaa   1920
tctcccactt tcaccagtta ttcactccgc acttggctac tcagtgtctt gctatgggca   1980
cgaaaactgg ttcgccgaat taaaacacac taaatgaatg gataaaactt atagcatcga   2040
```

<210> SEQ ID NO 4
<211> LENGTH: 419
<212> TYPE: PRT
<213> ORGANISM: Capsicum annuum

<400> SEQUENCE: 4

```
Met Ser Val Ala Leu Leu Trp Val Val Ser Pro Cys Asp Val Ser Asn
1               5                   10                  15

Gly Thr Gly Phe Leu Val Ser Val Arg Glu Gly Asn Arg Ile Phe Asp
            20                  25                  30

Ser Ser Gly Arg Arg Asn Leu Ala Cys Asn Glu Arg Ile Lys Arg Gly
        35                  40                  45

Gly Gly Lys Gln Arg Trp Ser Phe Gly Ser Cys Leu Gly Gly Ala Gln
    50                  55                  60

Thr Gly Ser Gly Arg Lys Phe Ser Val Arg Ser Ala Ile Val Ala Thr
65                  70                  75                  80

Pro Ala Gly Glu Met Thr Met Ser Ser Glu Arg Met Val Tyr Asp Val
                85                  90                  95

Val Leu Arg Gln Ala Ala Leu Val Lys Arg Gln Leu Arg Ser Thr Asp
            100                 105                 110

Glu Leu Asp Val Lys Lys Asp Ile Pro Ile Pro Gly Thr Leu Gly Leu
        115                 120                 125

Leu Ser Glu Ala Tyr Asp Arg Cys Ser Glu Val Cys Ala Glu Tyr Ala
    130                 135                 140

Lys Thr Phe Tyr Leu Gly Thr Met Leu Met Thr Pro Glu Arg Arg Lys
145                 150                 155                 160
```

```
Ala Ile Trp Ala Ile Tyr Val Trp Cys Arg Arg Thr Asp Glu Leu Val
                165                 170                 175

Asp Gly Pro Asn Ala Ser His Ile Thr Pro Ala Ala Leu Asp Arg Trp
            180                 185                 190

Glu Asp Arg Leu Glu Asp Val Phe Ser Gly Arg Pro Phe Asp Met Leu
        195                 200                 205

Asp Ala Ala Leu Ser Asp Thr Val Ser Lys Phe Pro Val Asp Ile Gln
    210                 215                 220

Pro Phe Arg Asp Met Ile Glu Gly Met Arg Met Asp Leu Arg Lys Ser
225                 230                 235                 240

Arg Tyr Arg Asn Phe Asp Glu Leu Tyr Leu Tyr Cys Tyr Tyr Val Ala
                245                 250                 255

Gly Thr Val Gly Leu Met Ser Val Pro Ile Met Gly Ile Ala Pro Glu
            260                 265                 270

Ser Lys Ala Thr Thr Glu Ser Val Tyr Asn Ala Ala Leu Ala Leu Gly
        275                 280                 285

Ile Ala Asn Gln Leu Thr Asn Ile Leu Arg Asp Val Gly Glu Asp Ala
    290                 295                 300

Arg Arg Gly Arg Val Tyr Leu Pro Gln Asp Glu Leu Ala Gln Ala Gly
305                 310                 315                 320

Leu Ser Asp Glu Asp Ile Phe Ala Gly Arg Val Thr Asp Lys Trp Arg
                325                 330                 335

Ile Phe Met Lys Lys Gln Ile Gln Arg Ala Arg Lys Phe Phe Asp Glu
            340                 345                 350

Ala Glu Lys Gly Val Thr Glu Leu Ser Ala Ala Ser Arg Trp Pro Val
        355                 360                 365

Leu Ala Ser Leu Leu Leu Tyr Arg Arg Ile Leu Asp Glu Ile Glu Ala
    370                 375                 380

Asn Asp Tyr Asn Asn Phe Thr Lys Arg Ala Tyr Val Ser Lys Pro Lys
385                 390                 395                 400

Lys Leu Ile Ala Leu Pro Ile Ala Tyr Ala Lys Ser Leu Val Pro Ser
                405                 410                 415

Thr Arg Thr

<210> SEQ ID NO 5
<211> LENGTH: 1497
<212> TYPE: DNA
<213> ORGANISM: Capsicum annuum

<400> SEQUENCE: 5
atggaaaccc ttctaaagcc ttttccatct cctttacttt ccattcctac tcctaacatg      60
tatagtttca acacaactc cacttttcca aatccaacca acaaaaaga ttcaagaaag       120 ttccattata gaaacaaaag cagtacacat ttttgtagct ttcttgattt agcacccaca      180
tcaaagccag agtctttaga tgttaacatc tcatggggttg atactgatct ggaccgggct    240
gaattcgacg tgatcatcat tggaactggc cctgccgggc ttcggctagc tgaacaagtt    300
tctaaatatg gtattaaggt atgttgcgtt gacccttcac cactttccat gtggccaaat    360
aattatggtg tttgggttga tgagtttgaa aagttgggat tagaagattg tctagatcat    420
aagtggcctg tgagttgtgt tcatataagt gatcacaaga ctaagtattt ggacagacca    480
tatggtagag taagtagaaa gaagttgaag ttgaaattgt tgaatagttg tgttgaaaat    540
agagtgaagt tttataaagc caaggttttg aaagtgaagc atgaagaatt tgagtcttcg    600
```

```
attgtttgtg atgatggtag gaagataagt ggtagcttga ttgttgatgc aagtggctat      660
gctagtgatt ttatagagta tgacaagcca agaaaccatg gttatcaagt tgctcatggg      720
attttagcag aagttgataa tcatccattt gatttggata aaatgatgct tatggattgg      780
agggattctc atttaggtaa tgagccatat ctgagggtga agaatactaa agaaccaaca      840
ttcttgtatg caatgccatt tgataggaat ttggtattct tggaagagac ttccttagtg      900
agtcggccta tgttatcgta tatggaagtg aaaagaagga tggtagcaag attaagacat      960
ttggggatca aagtgagaag tgtccttgag gaagagaagt gtgtgatcac tatgggagga     1020
ccacttccgc ggattcctca aaatgttatg gctattggtg ggacttcagg gatagttcat     1080
ccatcgtctg ggtacatggt ggctcgtagc atggcattgg caccagtact ggctgaggcc     1140
atcgtcgaaa gccttggctc aacaagaatg ataagagggt ctcaaccttta ccatagagtt     1200 tggaatggtt tgtggccttc ggatagaaga cgtgttagaa atgttattg tttcggaatg      1260 gagactttgt tgaagcttga tttgaaggt actaggagat tgtttgatgc tttcttgat      1320 gttgatccca agtactggca cgggttcctt tcttcaagat tgtctgtcaa agaacttgct     1380
gtactcagtt tgtacctttt tggacatgcc tctaatttgg ctaggttgga tattgttaca     1440
aagtgcactg tccccttggt taaactgctg ggcaatctag caatagagag cctttga       1497
```

<210> SEQ ID NO 6
<211> LENGTH: 497
<212> TYPE: PRT
<213> ORGANISM: Capsicum annuum

<400> SEQUENCE: 6

Met Glu Thr Leu Leu Lys Pro Phe Pro Ser Pro Leu Leu Ser Ile Pro
1               5                   10                  15

Thr Pro Asn Met Tyr Ser Phe Lys His Asn Ser Thr Phe Pro Asn Pro
            20                  25                  30

Thr Lys Gln Lys Asp Ser Arg Lys Phe His Tyr Arg Asn Lys Ser Ser
        35                  40                  45

Thr His Phe Cys Ser Phe Leu Asp Leu Ala Pro Thr Ser Lys Pro Glu
    50                  55                  60

Ser Leu Asp Val Asn Ile Ser Trp Val Asp Thr Asp Leu Asp Arg Ala
65                  70                  75                  80

Glu Phe Asp Val Ile Ile Ile Gly Thr Gly Pro Ala Gly Leu Arg Leu
                85                  90                  95

Ala Glu Gln Val Ser Lys Tyr Gly Ile Lys Val Cys Cys Val Asp Pro
            100                 105                 110

Ser Pro Leu Ser Met Trp Pro Asn Asn Tyr Gly Val Trp Val Asp Glu
        115                 120                 125

Phe Glu Lys Leu Gly Leu Glu Asp Cys Leu Asp His Lys Trp Pro Val
    130                 135                 140

Ser Cys Val His Ile Ser Asp His Lys Thr Lys Tyr Leu Asp Arg Pro
145                 150                 155                 160

Tyr Gly Arg Val Ser Arg Lys Leu Lys Leu Lys Leu Leu Asn Ser
                165                 170                 175

Cys Val Glu Asn Arg Val Lys Phe Tyr Lys Ala Lys Val Leu Lys Val
            180                 185                 190

Lys His Glu Glu Phe Glu Ser Ser Ile Val Cys Asp Asp Gly Arg Lys
        195                 200                 205

Ile Ser Gly Ser Leu Ile Val Asp Ala Ser Gly Tyr Ala Ser Asp Phe
    210                 215                 220

-continued

```
Ile Glu Tyr Asp Lys Pro Arg Asn His Gly Tyr Gln Val Ala His Gly
225                 230                 235                 240

Ile Leu Ala Glu Val Asp Asn His Pro Phe Asp Leu Asp Lys Met Met
            245                 250                 255

Leu Met Asp Trp Arg Asp Ser His Leu Gly Asn Glu Pro Tyr Leu Arg
        260                 265                 270

Val Lys Asn Thr Lys Glu Pro Thr Phe Leu Tyr Ala Met Pro Phe Asp
    275                 280                 285

Arg Asn Leu Val Phe Leu Glu Glu Thr Ser Leu Val Ser Arg Pro Met
290                 295                 300

Leu Ser Tyr Met Glu Val Lys Arg Arg Met Val Ala Arg Leu Arg His
305                 310                 315                 320

Leu Gly Ile Lys Val Arg Ser Val Leu Glu Glu Lys Cys Val Ile
            325                 330                 335

Thr Met Gly Gly Pro Leu Pro Arg Ile Pro Gln Asn Val Met Ala Ile
            340                 345                 350

Gly Gly Thr Ser Gly Ile Val His Pro Ser Ser Gly Tyr Met Val Ala
        355                 360                 365

Arg Ser Met Ala Leu Ala Pro Val Leu Ala Glu Ala Ile Val Glu Ser
370                 375                 380

Leu Gly Ser Thr Arg Met Ile Arg Gly Ser Gln Leu Tyr His Arg Val
385                 390                 395                 400

Trp Asn Gly Leu Trp Pro Ser Asp Arg Arg Arg Val Arg Glu Cys Tyr
            405                 410                 415

Cys Phe Gly Met Glu Thr Leu Leu Lys Leu Asp Leu Glu Gly Thr Arg
            420                 425                 430

Arg Leu Phe Asp Ala Phe Phe Asp Val Asp Pro Lys Tyr Trp His Gly
        435                 440                 445

Phe Leu Ser Ser Arg Leu Ser Val Lys Glu Leu Ala Val Leu Ser Leu
    450                 455                 460

Tyr Leu Phe Gly His Ala Ser Asn Leu Ala Arg Leu Asp Ile Val Thr
465                 470                 475                 480

Lys Cys Thr Val Pro Leu Val Lys Leu Leu Gly Asn Leu Ala Ile Glu
            485                 490                 495

Ser

<210> SEQ ID NO 7
<211> LENGTH: 101
<212> TYPE: DNA
<213> ORGANISM: Capsicum annuum

<400> SEQUENCE: 7
agggtgctga tcaagatgca gcattgttag ctagcaggct cgaaaagagg yctaataaca     60
cgcttggctc gcagctttct tttcatctga ggcaagtttc c                        101

<210> SEQ ID NO 8
<211> LENGTH: 101
<212> TYPE: DNA
<213> ORGANISM: Capsicum annuum

<400> SEQUENCE: 8
aactgaccct caaagcaaaa catcagcagc atcaactagc caaccccata ycaaatcaac     60
tggaaaaact gtattaccca agaaccctc tgcaaaaatt g                         101
```

<210> SEQ ID NO 9
<211> LENGTH: 136
<212> TYPE: DNA
<213> ORGANISM: Capsicum annuum

<400> SEQUENCE: 9

```
aatatatata tatatatata tatataggtg gcaaggctat ttggaccagc tatatttgaa    60
gcatcaaagt tgaaggtact tttctttggg agttgatgag aaaaagcacc caggaaagtt   120
gccaagaaca tataca                                                   136
```

<210> SEQ ID NO 10
<211> LENGTH: 19
<212> TYPE: DNA
<213> ORGANISM: Capsicum annuum

<400> SEQUENCE: 10

```
gagggtcacc agtgatacg                                                 19
```

<210> SEQ ID NO 11
<211> LENGTH: 24
<212> TYPE: DNA
<213> ORGANISM: Capsicum annuum

<400> SEQUENCE: 11

```
gcctgtgcta attcatcttg aggc                                           24
```

<210> SEQ ID NO 12
<211> LENGTH: 996
<212> TYPE: DNA
<213> ORGANISM: Capsicum annuum

<400> SEQUENCE: 12

```
cacaactcct ctttaagttt ctactcattc tctttgccaa ctttgatcaa aaacacctta    60
taataaattg atcaagattc aaggagtttt gggtacccaa tttcttgatg aaatggggac   120
tttgactgct tctctagtag ctccatctaa gctcaaccct gaaaagcata gctctctttt   180
tgtatacaaa actagaagaa agtcccacaa gaatcaatcc atagtccctg tggcaaggct   240
atttggacca gctatatttg aagcatcaaa gttgaaggta cttttctttg ggagttgatg   300
agaaaaagca cccaggaaag ttgccaagaa catatacact gactcatagt gatattactt   360
ctaaactcac tttggcaatc tctcaaacca tcaataactc tcagttgcaa ggttggtata   420
atagacttca aagggatgaa gtggttgcag aatggaagaa agttaaaggg aagatgtcac   480
tccatgtaca ttgccacatt agtggaggcc attttatgtt agacttattt gctagactca   540
gatactatat cttctgcaaa gaactccctg tggttctgaa ggcttttgtt catggagatg   600
agaatttact aaagaattat ccagagttgc aacaagcttt agtttgggta tattttcact   660
caaacattca agaattcaac aaagtagaat gttggggccc actcaaagat gcagcctccc   720
cctcatcaag tggggtaggt gggggtatga atacaagttt tacaagcaat agcaacatca   780
agtggaattt accaaagcct tgtgaagaga cttgtacatg ttgctttccc ccaatgagtg   840
ttatcccttg gccttctact actaatgtgg aaaatgggac catacaacaa ggcttgcaag   900
agcagcaaag ctgaaaaaag acagtaattc tgttgcttta ttatgtgatt tgatgtaatt   960
aattaattaa ttaattatca tcattatagg gtttgt                             996
```

<210> SEQ ID NO 13
<211> LENGTH: 26
<212> TYPE: DNA

```
<213> ORGANISM: Capsicum annuum

<400> SEQUENCE: 13
tttgggagtt gatgagaaaa agcacc                                          26
```

QUALITY AND PERMANENCE OF GREEN COLOR OF PEPPERS AT MATURITY AND OVER-MATURITY

FIELD OF THE INVENTION

The present invention relates to *Capsicum* plants producing fruits which maintain a green color at maturity and over-maturity and to methods of producing said plants. The invention also relates to seeds and plant parts, especially fruits, of said *Capsicum* plants, and to their use.

BACKGROUND OF THE INVENTION

Fruits of plants of the genus *Capsicum*, i.e. peppers, can display a wide variety of colors like red, brown, yellow, orange, green, white, lilac or purple. The color of pepper fruits is the result of a mixture of different pigments in the fruit, which are themselves controlled by a number of genes, certain of which have been characterized.

Green color of immature fruits is provided by the presence of chloroplasts containing green chlorophyll. During fruit ripening, the green color is degraded due to the breakdown of chlorophyll to colorless products. A gene, called cl ("chlorophyll retainer") has been shown to interfere with this breakdown. The cl gene encodes the *Capsicum* stay-green (CaSGR) protein (Borovsky and Paran, Theor Appl Genet (2008) 117:235-240).

The red and yellow color of mature pepper fruits result from the presence of carotenoids, such as capsanthin and capsorubin (red pigments) and violaxanthin and zeaxanthin (yellow pigments). At least three genes are known to be implied in the carotenoid pathway: y, c1 and wt (Hurtado-Hernandez, H., & Smith, P. G. Journal of Heredity (1985), 76(3), 211-213; Thorup, T. A., et al. PNAS 97.21 (2000): 11192-11197). The y gene encodes the capsanthin-capsorubin synthase (CCS) protein. The wt gene (also called c2) encodes the phytoene synthase (PSY) protein. To date, the identity of the c1 gene remains unknown.

Loss of function of the cl gene (i.e. genetically identified as clcl) induces a permanent green color of pepper at maturity. When the y gene is not functional (i.e. genetically identified as yy), the capsanthin and capsorubin responsible for the red color are no longer synthetized, thereby leading to a yellow color in pepper. When the wt gene is not functional (i.e. genetically identified as wtwt), it affects very early the carotenoid biosynthetic pathway and is thus responsible for a white color of the pepper (permawhite peppers).

The genetic combination clclyy in pepper is known to be responsible for a so-called permanent green color, with the clcl genotype allowing a continuous synthesis of chlorophyll (WO2004/089067). However, the color of the pepper fruits having this genotype, combined with dominant wild-type alleles for the wt gene (clclyyWTWT) turns into olive-green at maturity and over-maturity (Hurtado-Hernandez and Smith, 1985). This olive-green color may be undesirable for commercial reasons, as yellowing of green fruits is generally perceived negatively by consumers and, for this reason, consumers generally prefer fruits which exhibit a green color which does not display any yellowing.

To date, the known "permagreen" pepper varieties, i.e. varieties which are intended to stay green at maturity, such as the Evergreen or Sweet Green varieties contain the genetic combination clclyyWTWT, and thus develop the undesired olive-green color at maturity or over-maturity.

Accordingly, there exists a need for pepper plants producing fruits which are and stay green at maturity, and do not develop an olive-green color, neither at maturity, nor after maturity.

SUMMARY OF THE INVENTION

To obtain a permagreen pepper which stays green at maturity or over-maturity, and does not display an olive-green color, the inventors crossed a permagreen pepper having the genotype clclWTWT (leading to an olive-green color of the fruit at maturity) with a permawhite pepper having the genotype ClClwtwt. Plants with the genotype clclwtwt have been identified by the inventors in F2 plant populations, with fruits having unexpectedly a green color at maturity and over-maturity that is significantly different from the olive-green color of existing permagreen varieties, such as the Sweet Green variety or the permagreen parent.

Accordingly, the present invention relates to pepper plants which are genetically clclwtwt, and produce fruits which are and stay green and do not turn olive-green at maturity and/or over-maturity.

Unexpectedly, the inventors also found that crossing the permagreen and the permawhite parents led to the production of a high percentage of blind plants. Blindness, also called shoot apical meristem arrest, is a developmental abnormality observed in some plant species, including brassicas, tomato and pepper (de Jonge et al, 2018; Wetzstein et al, 2002). Blind plants can be characterized by an abnormal development of the plantlets, including plantlets without apical shoot and leaves or plantlets with very few (e.g. one to five, preferably one or two) true leaves that are often distorted and reduced in size. The inventors identified a QTL on chromosome 8, responsible for 22% of the blind phenotype at the plantlet stage, in this breeding scheme. The presence of heterozygous alleles at this QTL is associated with an increased susceptibility to the blind phenotype whilst, conversely, the presence of homozygous alleles at this QTL is associated with a reduced susceptibility to the blind phenotype.

Accordingly, the present invention also relates to pepper plants which comprise homozygous alleles at a QTL on chromosome 8, said QTL being associated to the development of a blind phenotype in plants.

The invention also relates to cells, parts and seeds of pepper plants of the invention, as well as methods for producing such plants or their progeny and methods for identifying such plants. The invention also relates to pepper fruits which are and stay green at maturity and over-maturity, and do not turn olive-green at maturity and over-maturity. The invention also relates to the use of said pepper fruits.

DEFINITIONS

Figure 1:
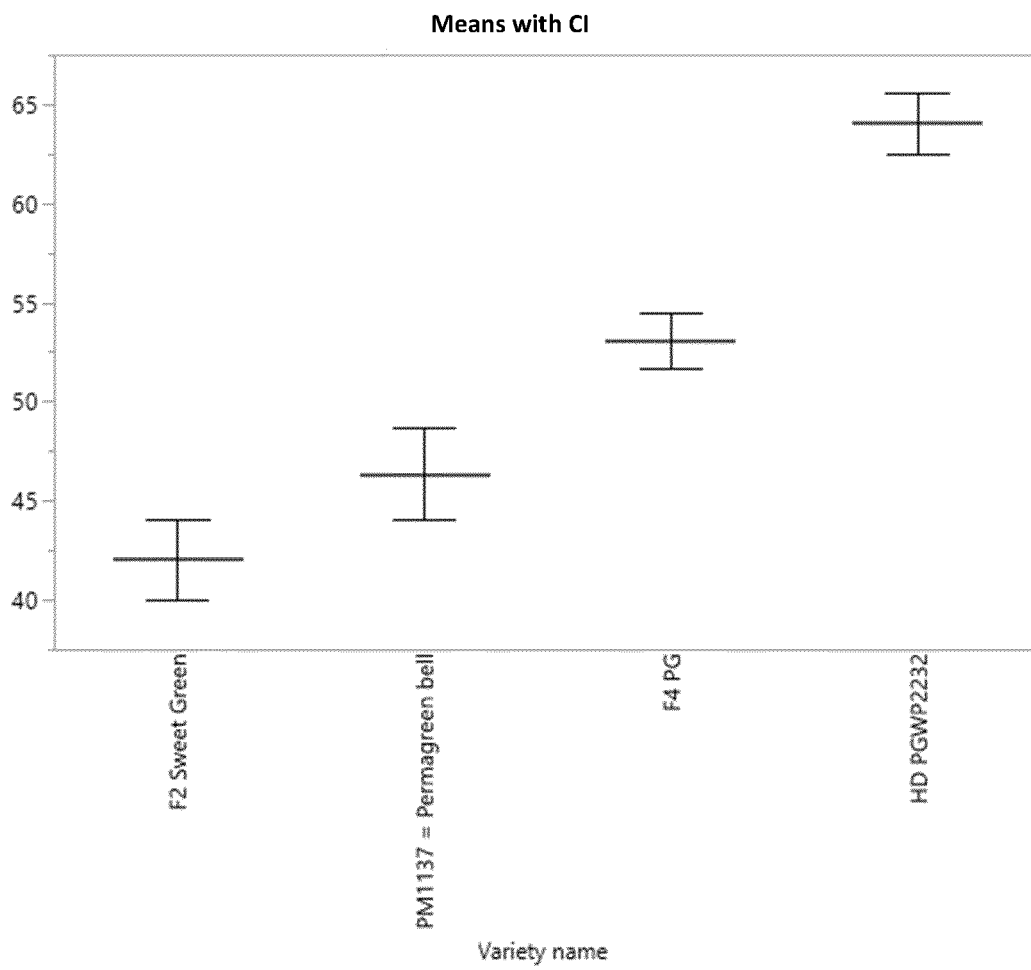
FIG. 1: Panel A shows the mean R (red) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.
Figure 2:
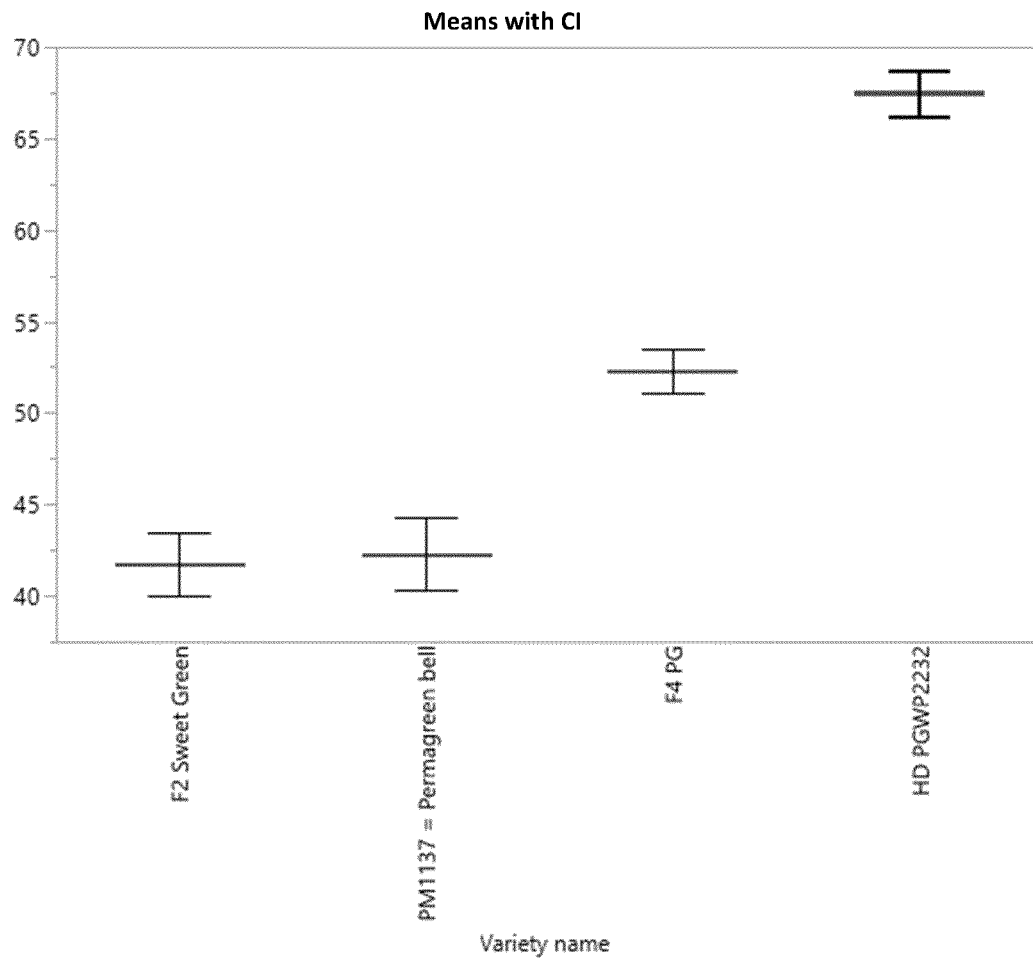
FIG. 2: Panel A shows the mean G (green) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.
Figure 3:
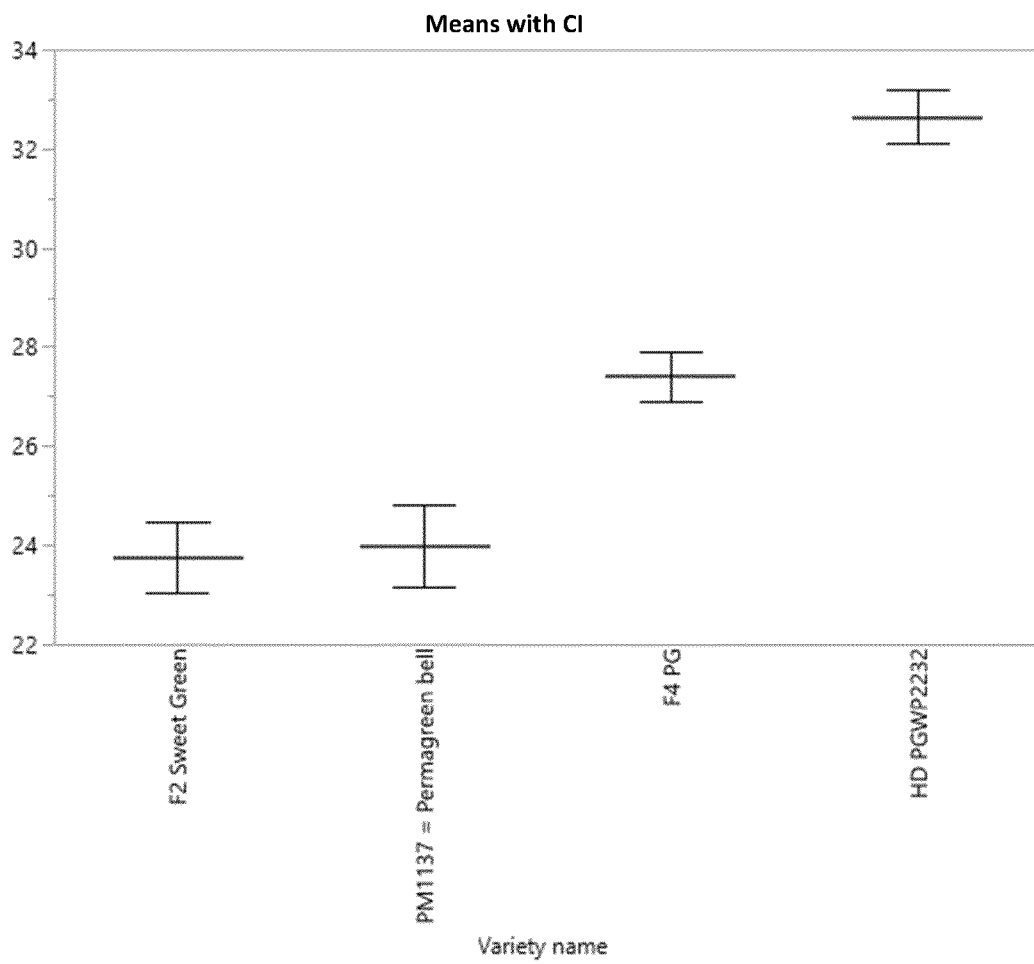
FIG. 3: Panel A shows the mean B (blue) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.
Figure 4:
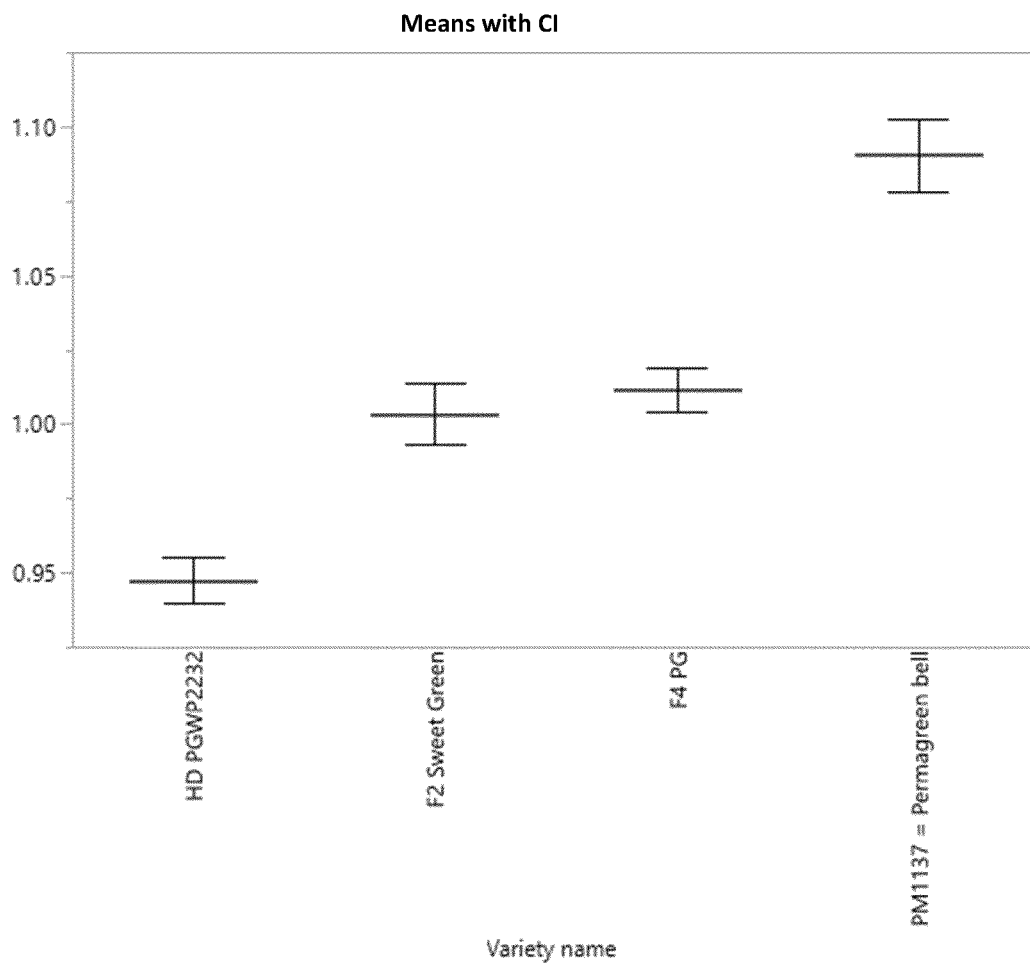
FIG. 4: Panel A shows the mean R/mean G (red/green) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.

As used herein, an "allele" refers to any of several alternative or variant forms of a genetic unit, such as a gene, which are alternative in inheritance because they are positioned at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

As used herein, the terms "blind" or "blind phenotype", refer to a plantlet which has its 2 cotyledons but no apex or a plantlet which has only one or two leaves growing from the apex, the leaf or leaves being thicker than normal leaves and/or their shape being abnormal. In the context of the present invention, a plant is considered as a blind plant when it exhibits a blind phenotype at the plantlet stage, even if the plant then starts again a normal growth and become a normal adult plant which, for instance, sets fruits. Certain plants exhibit the blind phenotype temporarily, for instance only at the plantlet stage, whilst other plants keep the blind phenotype for their whole life, which means that said plants never develop and set fruits.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "genetic determinant" and/or "QTL" refers to any segment of DNA associated with a biological function. Thus, QTLs and/or genetic determinants include, but are not limited to, genes, coding sequences and/or the regulatory sequences required for their expression. QTLs and/or genetic determinants can also include non-expressed DNA segments that, for example, form recognition sequences for other proteins.

As used herein, the term "genotype" refers to the genetic makeup of an individual cell, cell culture, tissue, organism (e.g., a plant), or group of organisms.

As used herein, the term "heterozygote" refers to a diploid or polyploid individual cell or plant having different alleles (forms of a given gene, genetic determinant or sequences) present at least at one locus.

As used herein, the term "heterozygous" refers to the presence of different alleles (forms of a given gene, genetic determinant or sequences) at a particular locus.

As used herein, "homologous chromosomes", or "homologs" (or homologues), refer to a set of one maternal and one paternal chromosomes that pair up with each other during meiosis. These copies have the same genes in the same loci and the same centromere location.

As used herein, the term "homozygote" refers to an individual cell, or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue, plant part or or plant resulting from a cross between parents that differ in one or more genes.

As used herein, the term "linkage" or "genetic linkage" or "association" refers to the tendency of alleles at different loci on the same chromosome to segregate together more often than would be expected by chance if their transmission were independent, in some embodiments as a consequence of their physical proximity. As used herein, the term "linkage drag" refers to the inheritance of undesirable donor alleles in the same genomic region as a target locus.

As used herein, the term "locus" (plural: "loci") refers to any site that has been defined genetically, this can be a single position (nucleotide) or a chromosomal region. A locus may be a gene, a genetic determinant, or part of a gene, or a DNA sequence, and may be occupied by different sequences. A locus may also be defined by a SNP (Single Nucleotide Polymorphism), by several SNPs, or by two flanking SNPs.

As used herein, a "loss-of-function mutation", or "inactivating mutation", is a mutation which results in the gene product having a reduced function or no function at all (being partially or wholly inactivated). When the allele has a complete loss of function, it is also called a null allele. Phenotypes associated with such mutations are generally recessive.

As used herein, a "marker" is an indicator for the presence of at least one phenotype or genotype. Typically a marker is a detectable polymorphism. Markers include, but are not limited to, single nucleotide polymorphisms (SNPs), small to large insertions and deletions, chromosomal rearrangements, cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A "nucleic acid marker" means a nucleic acid molecule that is capable of being a marker for detecting a polymorphism, phenotype, or both associated with a trait of interest.

As used herein, "marker-based selection" or "marker-assisted selection (MAS)" or "marker-assisted breeding (MAB)" refers to the use of genetic markers to detect one or more nucleic acids from a plant, wherein the nucleic acid is associated with a desired trait to identity plants that carry genes for desirable (or undesirable) traits, so that those plants can be used (or avoided) in a selective breeding program.

As used herein, "maturity" is a stage of pepper fruit growth. Maturity corresponds to a stage where the fruit has reached its fully expanded size with optimal firmness, and produces seeds capable to germinate. Maturity follows "immaturity", where seeds are not yet capable to germinate, and precedes "over-maturity" where the fruits begin to shrivel and become softer. A person skilled in the art will readily recognize mature fruits visually and by touching them and assessing their firmness. A fruit comprising wild type alleles of the CI gene, i.e. which degrades chlorophyll during maturation, is said to be mature when its colour turns from green to red. For a specific fruit, the period of time that has elapsed since fruit setting can be used as an indication of fruit maturity. For instance, two fruits of a same fixed variety can be considered to be at the same stage of maturity when they have originally set at the same time and they have grown under the same conditions, in particular at the same height. Preferably, maturity corresponds to a period between 65 weeks and 90 weeks after fruit setting.

As used herein, the term "offspring" or "progeny" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "pepper" means any species, variety, cultivar, or population of the *Capsicum* genus.

As used herein, a single nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T.

DETAILED DESCRIPTION OF THE INVENTION

The inventors have crossed pepper plants in order to combine recessive alleles for the cl gene and recessive alleles for the wt gene. They have unexpectedly obtained pepper plants which produce green fruits at maturity and over-maturity, said green color being markedly different from the olive-green color of existing permagreen varieties, such as the Sweet Green or Evergreen varieties. These improved permagreen peppers having a clclwtwt genotype have been called "PermagreenWhite" or "PGW" peppers by the inventors.

Accordingly, in a first aspect, the invention relates to a *Capsicum* plant which produces fruits which are green at maturity and/or over-maturity, i.e. which are not olive-green at maturity and/or over-maturity, wherein said plant homozygously comprises in its genome:
(a) a mutant allele of the cl gene encoding the *Capsicum* stay-green (CaSGR) protein, and
(b) a mutant allele of the wt gene encoding the phytoene synthase (PSY) protein.

The cl gene has been mapped to chromosome 1 of the pepper genome, and shown to encode the *Capsicum* stay-green (CaSGR) protein (Borovsky and Paran, Theor Appl Genet (2008) 117:235-240). A mRNA sequence of a non-mutant (wild-type) allele of the cl gene has been deposited in Genbank under accession NM_001324918.1 (update Dec. 23, 2018), wherein the cds is positioned between nucleotides 113 and 913. The coding sequence of the wild-type cl gene is set forth in SEQ ID NO: 1. The translated sequence, i.e. the amino acid sequence of the CaSGR protein has been deposited in Genbank under accession NP_001311847.1 (update Dec. 23, 2018), as set forth in SEQ ID NO: 2.

In one embodiment, the mutant allele of the cl gene, differs from the wild-type sequence of the gene (its coding sequence being set forth in SEQ ID NO: 1) by at least one nucleotide substitution, insertion or deletion in said sequence. The mutant allele of the cl gene can also differ from the wild-type sequence of the cl gene by the insertion or the deletion of one or more nucleic acid segments, including the deletion of the full gene. Preferably, the mutant cl allele is a loss-of-function allele, i.e. it comprises a loss-of-function mutation. The mutation may induce one or more amino acid substitutions in the sequence of the CaSGR protein, and impair the function of the CaSGR protein. In one embodiment, the loss-of-function mutation in the cl gene is a null mutation. A null mutation prevents expression of an active CaSGR protein, for instance by causing a premature stop in the translation of the mRNA into a protein, resulting into the expression of a truncated form of the CaSGR protein. According to one aspect, the mutant cl allele in the *Capsicum* plant according to the invention comprises an inserted thymine between the cytosine in position 174 and the thymine in position 175 of the wild-type coding sequence of the cl gene, e.g. as set forth in SEQ ID NO: 1. This Insertion/Deletion (InDel) polymorphism C[T]T, corresponding to SEQ ID NO:12, has been identified by the present inventors in the parent permagreen line (F4 PG) used to produce the Permagreen White plants of the invention. Said mutation induces a frameshift, thereby introducing a premature stop codon in the cl sequence, leading to a truncated form of the CaSGR protein. An exemplary cl mutant allele, comprising the C[T]T Indel between positions 174 and 175 of the coding sequence of the cl gene, is present in representative mutant *Capsicum* seeds deposited on Jul. 26, 2018, under accession number 43123, at NCIMB Ltd, Ferguson Building, Craibstone Estate, Bucksburn, Aberdeen, AB21 9YA, Scotland, UK. Mutant alleles and corresponding markers can be identified by methods known in the art, such as but not limited to RFLP (Restriction Fragment Length Polymorphism) or RAPD (Random Amplified Polymorphic DNA).

The wt gene has been mapped to chromosome 4 of the pepper genome, and shown to encode the Phytoene Synthase enzyme. A coding nucleic acid sequence of a non-mutant (wild-type) allele of the wt gene has been deposited in Genbank under accession number NM_001324967 (update Sep. 29, 2018), and is set forth in SEQ ID NO: 3. The translated sequence, i.e. amino acid sequence of the PSY protein encoded by the wt gene has been deposited in Genbank under accession number NP_001311896.1 (update Sep. 29, 2018) and is set forth in SEQ ID NO: 4. In one embodiment, the mutant allele of the wt gene differs from the wild-type sequence of the wt gene (its coding sequence being set forth in SEQ ID NO:3) by at least one nucleotide substitution, insertion or deletion in said sequence, in particular wherein said nucleotide substitution, insertion or deletion impairs the function or prevent expression of the PSY protein. The mutant allele can also differ from the wild-type sequence of the wt gene by the insertion or the deletion of one or more nucleic acid segments, including the deletion of a portion of the wt gene or of the full gene. Preferably, the mutant wt allele is a loss-of-function allele, i.e. it comprises a loss-of-function mutation. The mutation may induce one or more amino acid substitutions in the sequence of the PSY protein, and impair the function of the PSY protein. Still preferably, the loss-of-function mutation is a null mutation. A null mutation prevents expression of an active PSY protein. An example of wt mutation is described in Kim, Ok Rye, et al., Molecules and cells 30.6 (2010): 569-574, which discloses a splicing mutation (A to C) in position 2683 of the genomic sequence of the psy gene, at the end of the $6^{th}$ intron, causing aberrant splicing, and premature translation termination of Habanero pepper PSY protein. A preferred wt mutant allele according to the invention is comprised in representative seeds deposited at NCIMB under accession number 43123. According to one embodiment, said mutant allele of the wt gene can be detected by detecting the presence or absence of a specific marker, e.g. a SCAR marker detected by PCR using the nucleic acid primers as set forth in SEQ ID NO: 10 and SEQ NO: 11. In one embodiment, when detected by PCR using the nucleic acid primers as set forth in SEQ ID NO: 10 and SEQ NO: 11, a wild type wt allele yields a 1207 bp (gDNA) or 351 bp (cDNA) fragment. In one embodiment, there is no amplified fragment for a mutant wt allele.

According to a further aspect of the invention, the *Capsicum* plant according to the invention homozygously comprises in its genome a mutant allele of the y gene encoding the capsanthin-capsorubin synthase (CCS) protein. The coding nucleic acid sequence of a non-mutant allele of the y gene is set forth in SEQ ID NO: 5 (Genbank accession NM_001325069, update Dec. 22, 2018). The amino acid sequence of the CCS protein encoded by the y gene has been deposited in Genbank under accession number NP_001311998.1 (update Dec. 22, 2018) and is set forth in SEQ ID NO: 6. In one embodiment, the mutant allele of the y gene differs from the wild-type sequence of the y gene (its coding sequence being set forth in SEQ ID NO: 5) by at least one nucleotide substitution, insertion or deletion in said sequence. The mutant allele can also differ from the wild-type sequence of the y gene by the insertion or the deletion of one or more nucleic acid segments, including the deletion of the full gene. Preferably, the mutant y allele is a loss-of-function allele, i.e. it comprises a loss-of-function mutation. The mutation may induce one or more amino acid substitutions in the sequence of the CCS protein, and impair the function of the CCS protein. Still preferably, the loss-of-function mutation is a null mutation. A null mutation prevents expression of an active CCS protein. Examples of CCS mutations are those described in Lefebvre, Véronique, et al. *Plant molecular biology* (1998) 36(5): 785-789, where yellow fruits comprising a deletion of the y gene are disclosed. Another example of CCS mutation is described in LeKim, Jeong Eun, et al. Horticultural Science and Technology (2017) 35(5): 599-607, disclosing a nonsense mutation due to a T insertion at position 1026 of the coding region of the y gene. A preferred y mutant allele according to the invention is comprised in representative seeds deposited at NCIMB under accession number 43123.

The mutations in mutant cl, wt and y alleles can have a natural cause (spontaneous mutations) or can be induced via methods such as mutagenesis. Mutagenesis methods are known in the art and include chemical mutagenesis using ethyl methanesulfonate (EMS). Other chemical mutagenic agents include but are not limited to, diethyl sufate (des), ethyleneimine (ei), propane sultone, N-methyl-N-nitrosourethane (mnu), N-nitroso-N-methylurea (NMU), N-ethyl-N-nitrosourea (enu), and sodium azide.

Alternatively, the mutations can be induced by means of irradiation, which is for example selected from x-rays, fast neutrons, UV radiation.

Mutagenesis techniques can be followed by an identification method such as TILLING. TILLING (Targeting Induced Local Lesions IN Genomes) is a general reverse genetics technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as cl, wt and/or y according to the invention. S1 nucleases, such as CEL1 or ENDO1, are used to cleave heteroduplexes of mutant and wild type target DNA and detection of cleavage products using e.g. electrophoresis such as a LI-COR gel analyzer system, see e.g. Henikoff et al. Plant Physiology 2004, 135: 630-636. TILLING has been applied in many plant species, including pepper (Kang, H. S., Kim, S. H., Lee, S. W. et al. Hortic. Environ. Biotechnol. (2018) 59: 447). Also EcoTILLING, whereby mutants in natural populations are detected, has been widely used, see Till et al. 2006 (Nat Protoc 1: 2465-77) and Comai et al. 2004 (Plant J 37: 778-86).

In another embodiment of the invention, the mutations are induced by means of genetic engineering. The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated through the use of Zinc finger nuclease (ZFN) technology (ZFN-1, ZFN-2 and ZFN-3, see U.S. Pat. No. 9,145,565), Oligonucleotide directed mutagenesis (ODM), Cisgenesis and intragenesis, Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641), the CRIPSR/Cpf1 system, engineered meganuclease, engineered homing endonucleases, DNA guided genome editing (Gao et al., Nature Biotechnology (2016)), and Synthetic genomics. A major part of targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development".

Accordingly, the plants according to the invention may be obtained by different processes, and are not exclusively obtained by means of an essentially biological process.

In one embodiment, the cl, wt and/or y mutant alleles of the *Capsicum* plant according to the invention are obtainable from representative seeds deposited at the NCIMB, under accession number 43123. In particular, the cl, wt and/or y mutant alleles are obtainable by growing seeds deposited at the NCIMB, under accession number 43123, and crossing the plants derived from said seeds, with another *Capsicum* plant.

The PermagreenWhite plants according to the invention produce fruits which exhibit a green color at maturity and/or over-maturity (herein also referred to as the PermagreenWhite phenotype). In one embodiment, said green color of mature fruits can be distinguished from the color of fruits of existing varieties, at the same stage of maturity. In particular, the green color of mature fruits of plants of the invention can be distinguished from the color of fruits of existing permagreen varieties, such as the Evergreen or Sweet Green commercial varieties, at the same stage of maturity, e.g. hybrid peppers Evergreen 6203 or Evergreen 7181. As observed and measured by the inventors, the fruit color of existing permagreen pepper varieties can be qualified as olive-green at fruit maturity and over-maturity, corresponding to a green color exhibiting some yellowing. A difference of fruit color can be observed, assessed and/or measured by any method and/or means known in the art. In one embodiment, a difference of fruit colors, in particular between pepper of plants of the invention and peppers having a different genotype at the cl, wt and/or y locus, is observable with the naked eye. In another embodiment, the difference between fruit colors can be measured by digital image colorimetric analysis. In one embodiment, said analysis involves taking photographs of the fruits to be compared and determining and comparing the colorimetric data of each fruit, in particular the mean R, mean G and mean B (red, green, blue) values of each fruit, wherein R, G and B represent the color values of a pixel in a 8-bit color system. In this system, the color is encoded by 3 channels R, G and B, each with values 0 to 255. In one aspect, the mean R, mean G and mean B represent the average R, G and B values, respectively, measured for all pixels at the visible surface of a fruit, as photographed, or at least for a significant part of the visible surface. The average may be calculated over at least 500 pixels, preferably at least 1000 pixels, still preferably at least 2000 pixels, most preferably about 3000 pixels. In one aspect, the analysis also involves determining and comparing the mean R/mean G, mean G/mean B and mean R/mean B of the fruits to be compared. In one aspect, a color difference between two groups of fruits exists when there is a statistically significant difference between at least one of the values mean R, mean G, mean B, mean R/mean G, mean G/mean B and mean R/mean B, calculated over the fruits of each group. Preferably, there is a statistically significant difference on at least two of these values, still preferably at least three of these values, even preferably at least four of these values and even preferably at least five or all six of these values. A statistically significant difference can be assessed by any statistical test known in the art, for instance a one-way ANOVA followed by post-hoc Tukey's HSD test or Dunnett's test. Preferably, statistical significance is reached for a p value<0.05. For the purpose of establishing a statistically significant difference, at least 20 fruits, preferably at least 50 fruits, still preferably at least 100 fruits may be compared, by plant population.

The inventors determined the mean R, mean G, mean B, mean R/mean G, mean R/mean B and mean G/mean B values of fruits of plants of the invention, at fruit maturity, and compared them to various existing permagreen varieties, including the permagreen parent F4 PG, the PM1137 accession from which the F4 PG is derived, and a F2 Sweet Green population, at the same stage of fruit maturity. The inventors found statistically significant differences between the green color of PermagreenWhite fruits according to the invention and the olive green color of the different permagreen varieties tested, including the Sweet Green variety.

Accordingly, in one aspect of the invention, the *Capsicum* plant of the invention produces fruits which are green at maturity and/or over-maturity, wherein the green color of said fruits is different, at the same stage of fruit maturity, from the color of fruits of a second *Capsicum* plant which does not comprise at least one of the genetic determinants of the plants of the invention. In particular, said second *Capsicum* plant does not comprise homozygous mutant alleles at the cl and wt locus. In a further aspect, said second *Capsicum* plant homozygously comprises a mutant allele of the cl gene and comprises a non-mutant (wild-type) allele of the wt gene (i.e. said control plants have a clclWTWT genotype or clclWtwt genotype). In a further aspect, said second *Capsicum* plant homozygously comprises a mutant allele of the y gene. In yet a further aspect, said second *Capsicum* plant is from a variety known as "permagreen" which has a clclWtWT genotype, in particular the SweetGreen commercial variety or a progeny of a plant from the Sweet Green variety having the same genotype at the cl and wt loci, preferably at the y locus.

In one embodiment, the *Capsicum* plant according to the invention produces fruits which are green at maturity and/or over-maturity which, when analyzed using a RGB color model, have at least one, preferably at least two, still preferably at least three, even still preferably at least four, even more preferably at least five of their mean R, mean G, mean B, mean R/mean G, mean G/mean B which is statistically different from the corresponding variable of fruits from a control plant as defined in the present invention, at the same stage of maturity or over-maturity. Any combination of these variables can be statistically different from the corresponding variables in the compared fruits.

The F2 and F3 generation of PermagreenWhite plants obtained by the inventors comprised a significant proportion of blind plants (from 7 to 36%), whilst this phenotype was absent from the parent permagreen and permawhite lines, thereby revealing a possible linkage or pseudo-linkage between the genes responsible for the green color and the genetic determinants associated with the blind phenotype. A high proportion of blind plants may be an important drawback for pepper producers, as producers generally uproot blind plants as soon as signs of blindness appear, and thus have to sow new plants instead, thus reducing the yield of pepper production. It is thus desirable to provide genotypes with a reduced susceptibility to blindness, along with molecular tools allowing to identify and select seeds and plants with such reduced susceptibility.

In the present invention, the inventors have unexpectedly been able to break the linkage between the genes responsible for the green color and the genetic determinants associated with the blind phenotype, and have obtained PermagreenWhite plant populations comprising no blind plants at all. In one aspect, the present invention thus relates to a *Capsicum* plant of the invention, which does not exhibit a blind phenotype. In another aspect, the *Capsicum* plant according to the invention is capable of producing a population of progeny plants comprising less than 3%, preferably less than 1%, still preferably about 0% plants having a blind phenotype, e.g. by self-pollination. In another aspect, the invention relates to a population of seeds of *Capsicum* plants of the invention, wherein said seeds are capable of giving rise to a population of plants comprising less than 3%, preferably less than 1%, still preferably about 0% plants. The invention also relates to the plant population grown from said seeds. Reference seeds deposited at NCIMB under accession number 43123 are seeds from double haploid plants derived from a PermagreenWhite plant population comprising no blind plants, i.e. wherein the linkage between the genes for green color and the genetic determinants for the blind phenotype, has been broken.

The inventors identified a quantitative trait loci (QTL) on chromosome 8, responsible for 22% of the blind phenotype at the plantlet stage and 13% at the harvest stage. The QTL, if the plant is homozygous for one of its alleles, is associated with a reduced susceptibility to blind phenotype, whilst the presence of heterozygous alleles at the QTL is associated with an increased susceptibility to blind phenotype.

Accordingly, the *Capsicum* plant according to the invention preferably comprises homozygous alleles at a QTL on chromosome 8, wherein the presence of homozygous alleles at said QTL is associated with a reduced susceptibility to blind phenotype. In one aspect, said QTL is linked to each of the markers set forth in SEQ ID NO: 7 and SEQ ID NO: 8.

In a further aspect, the position of said QTL in the genome is delimited by each of the markers set forth in SEQ ID NO: 7 and SEQ ID NO: 8. In another aspect, said QTL is physically located between positions 132028868 and 132040163 of the reference genome *Capsicum annuum* Pepper Zunla 1 Ref_v1.0.

In one aspect, the *Capsicum* plant according to the invention comprises at least one of the following alleles in homozygous form:
allele G or A of the sequence set forth in SEQ ID NO: 7 and/or
allele G or A of the sequence set forth in SEQ ID NO: 8.

The allele G of the sequence set forth in SEQ ID NO: 7 corresponds to the sequence "AGGGTGCTGATCAA-GATGCAGCATTGT-TAGCTAGCAGGCTCGAAAAGAGGGCTAATAA CACGCTTGGCTCGCAGCTTTCTTTTCATCT-GAGGCAAGTTTCC" and the allele A of the sequence set forth in SEQ ID NO: 7 corresponds to the sequence "AGGGTGCTGATCAAGATGCAGCATTGT-TAGCTAGCAGGCTCGAAAAGAGGACTAATAA CACGCTTGGCTCGCAGCTTTCTTTTCATCT-GAGGCAAGTTTCC", said sequences differing by the presence of a G or A in position 51 of SEQ ID NO: 7.

The allele G of the sequence set forth in SEQ ID NO: 8 corresponds to the sequence "AACTGACCCT-CAAAGCAAAACATCAGCAGCATCAACTAGC-CAACCCCATAGCAAATCAA CTGGAAAAACTGTAT-TACCCAAAGAACCCTCTGCAAAAATTG" and the allele A of the sequence set forth in SEQ ID NO: 8 corresponds to the sequence "AACTGACCCT-CAAAGCAAAACATCAGCAGCATCAACTAGC-CAACCCCATAACAAATCAA CTGGAAAAACTGTAT-TACCCAAAGAACCCTCTGCAAAAATTG", said sequences differing by the presence of a G or A in position 51 of SEQ ID NO: 8.

In another aspect, the *Capsicum* plant according to the invention comprises homozygous alleles at the locus delimited by each of the markers set forth in SEQ ID NO: 7 and SEQ ID NO: 8 and/or at the locus situated between positions 132028868 and 132040163 of the reference genome *Capsicum annuum* Pepper Zunla 1 Ref_v1.0.

In a further aspect, the *Capsicum* plant according to the invention comprises homozygous alleles at a QTL on chromosome 8 in its genome, wherein the presence of homozygous alleles at said QTL is associated with a reduced susceptibility to blind phenotype, and wherein said alleles of said QTL are present, in homozygous form, in the genome of the seeds deposited at NCIMB under accession number 43123, in particular wherein said QTL is linked to each of the markers set forth in SEQ ID NO: 7 and SEQ ID NO: 8.

The *Capsicum* plant according to the invention can be from any species within the *Capsicum* genus. In particular, it may be a *Capsicum annuum, Capsicum baccatum, Capsicum frutescens, Capsicum chinense, Capsicum pubescens* or *Capsicum chacoense* plant. Preferably, the plant according to the invention is a *Capsicum annuum* plant, more preferably a sweet pepper or a hot pepper. The *Capsicum* plant can also be from any type, preferably from pepper types commonly harvested at the green stage. In particular, the *Capsicum* plant may be of one of the following types: Dulce Italiano, Lamuyo and blocky in China, Blocky Florida, Marconi, Jalapeno, Cayenne, Charleston or Sivri.

The *Capsicum* plant according to the invention may advantageously comprise one or more genes responsible for a trait of agronomic interest such as, but not limited to, genes that confer resistance to pests or disease, genes that confer resistance or tolerance to an herbicide, genes that control male sterility, genes that affect abiotic stress resistance (e.g., against salt, heavy metal, flooding), and other genes and transcription factors that affect plant growth and agronomic traits such as yield, flowering, plant growth or plant architecture, fruit growth, shape or taste or resistance to a pest or a disease. According to a particular aspect, it comprises at least one resistance to a pathogen selected from *Colletotrichum* spp., *Ralstonia solanacearum*, *Rhizoctonia solani*, *Pythium* spp, *Fusarium oxysporum*, *Phytophthora capsici*, *Sclerotium rolfsii*, *Verticillium albo-atrum*, *Verticillium dahliae*, *Meloidogyne incognita*, *Meloidogyne arenaria*, *Meloidogyne javanica*, *Meloidogyne hapla*, *Meloidogyne enterolobii*, *Leveillula taurica*, *Xanthomonas campestris*, viruses such as PMMV, TMV, TSWV, PVY, Geminivirus or CMV, or insects such as *thrips* (e.g. *Frankliniella occidentalis* and *Thrips parvispinus*).

In another embodiment, the *Capsicum* plant according to the invention is obtainable by breeding with a plant grown from a seed deposited at NCIMB under accession number 43123. In a further embodiment, the *Capsicum* plant according to the invention is obtainable by growing a plant from a seed deposited at NCIMB under accession number 43123.

In one embodiment, the *Capsicum* plant according to the invention is a plant from an inbred line. In another embodiment, the invention relates to a hybrid *Capsicum* plant. The hybrid plant is preferably obtainable by crossing a first *Capsicum* plant homozygously comprising in its genome:
(a) a mutant allele of the cl gene encoding the *Capsicum* stay-green (CaSGR) protein, and
(b) a mutant allele of the wt gene encoding the phytoene synthase (PSY) protein.

In an embodiment, the first *Capsicum* plant homozygously further comprises in its genome a mutant allele of the y gene encoding the capsanthin-capsorubin synthase (CCS) protein and a second *Capsicum* plant, different from the first plant.

The invention also relates to a progeny plant of a *Capsicum* plant of the invention.

In another embodiment, the *Capsicum* plant according to the invention is a haploid, dihaploid or double haploid plants. Haploid and double haploid plants can, for example, be produced by cell or tissue culture followed by the application of chromosome doubling agents and regeneration into a whole plant. For double haploid production, chromosome doubling may be induced using known methods, such as colchicine treatment or the like.

The invention also relates to a plant part of a *Capsicum* plant according to the invention, in particular seeds, explants, reproductive material, scion, cutting, seed, fruit, root, rootstock, pollen, ovule, embryo, protoplast, leaf, anther, stem, petiole or flowers.

In a particular aspect, the invention relates to a fruit or a population of fruits from *Capsicum* plants according to the invention, wherein said fruit(s) are green at maturity and/or over-maturity. In an embodiment, the color of said fruits is different from the color of fruits from a second *Capsicum* plant which does not comprise at least one of the genetic determinants of the plants of the invention, in particular a second *Capsicum* plant genetically clclWTWT, more particularly a permagreen variety, such as a Sweet Green or Evergreen variety, at the same stage of maturity. In particular, the color of the fruits of the invention is different from the color of the hybrid pepper 'Evergreen 6203' and/or 'Evergreen 7181', as described in U.S. Pat. No. 9,474,220 B2, wherein 'Evergreen 6203' is deposited in the American Type Culture Collection (ATCC), under ATCC number PTA-121139 and wherein 'Evergreen 7181' is deposited in the American Type Culture Collection (ATCC), ATCC Patent Depository under ATCC number PTA-121140. In particular, said fruit(s) have at least one of their mean R, mean G, mean B, mean R/mean G, mean G/mean B variables which is statistically different from the corresponding parameter of fruits from the second *Capsicum* plant, at the same stage of maturity. Preferably, said population of fruits comprises at least 10, 50, 100, 250, 500 or 1000 fruits.

The invention is also directed to a cell of the *Capsicum* plant according to the invention, preferably a cell derived from embryos, protoplasts, meristematic cells, callus, pollen, leaves, anthers, stems, petioles, roots, root tips, fruits, seeds, flowers, cotyledons, and/or hypocotyls of a plant according to the invention. Cells of the invention bear the genetic constituents of the pepper of the invention, in particular mutant alleles and/or QTL of the invention, preferably in homozygous form. The cell can be any type of *Capsicum* cell, including an isolated cell and/or a cell capable of regenerating a whole *Capsicum* plant, bearing the mutant alleles and/or QTL as described in the present invention.

The invention is also directed to a seed which can be grown into a *Capsicum* plant according to the invention. The invention is also directed to a population of seeds of the invention, preferably wherein said population comprises at least 50, 100, 250 or 500 seeds.

The present invention is also directed to a tissue culture of non-regenerable or regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and the cells contain mutant alleles of the cl and wt genes and optionally a mutant allele of the y gene, homozygously or heterozygously in their genome conferring, when present homozygously the improved phenotype, namely a green color of fruits at maturity and/or over-maturity.

The tissue culture will preferably be capable of regenerating plants having the physiological and morphological characteristics of the pepper plant from which it derives, and of regenerating plants having the same genotype or substantially the same genotype as the said pepper plant. The present invention also provides *Capsicum* plants regenerated from the tissue cultures of the invention.

The invention also provides a protoplast of the plant defined above, or from the tissue culture defined above, said protoplast containing the mutant alleles and/or QTL as described in the present invention.

According to an aspect, the present invention is also directed to the use of a vegetative plant part of a plant according to the invention for vegetative propagation. In other aspects, the invention is directed to a method for producing a *Capsicum* plant of the invention by vegetative propagation.

In certain embodiments, said use or method comprises the steps of: (a) obtaining a part of a plant according to the present invention; (b) vegetatively propagating said plant part to generate a plant from said plant part. In a further aspect, said use or method comprises: (i) collecting vegetative tissue capable of being propagated from a plant of the invention; (ii) cultivating said tissue to obtain proliferated shoots; and (iii) rooting said proliferated shoots to obtain rooted plantlets. In some of these aspects, the use or method further comprises growing plants from said rooted plantlets.

In another aspect, the invention is directed to a plant produced by vegetative propagation according to the aforementioned method.

In some embodiments, protoplast fusion can be used for the transfer of nucleic acids from a donor plant to a recipient plant. Protoplast fusion is an induced or spontaneous union, such as somatic hybridization, between two or more protoplasts (the cell walls are removed by enzymatic treatment) to produce a single bi- or multi-nucleate cell. The fused cell, which can even be obtained with plant species that cannot be interbred in nature, is tissue cultured into a hybrid plant exhibiting the desirable combination of traits. More specifically, a first protoplast can be obtained from a *Capsicum* plant according to the invention. A second protoplast can be obtained from a second *Capsicum* plant, preferably a plant line that comprises commercially valuable characteristics. The protoplasts are then fused using traditional protoplast fusion procedures, which are known in the art.

In further embodiments, embryo rescue can be employed in the cross of two *Capsicum* plants. Embryo rescue can be used as a procedure to isolate embryos from crosses wherein plants fail to produce viable seed. In this process, the fertilized ovary or immature seed of a plant is tissue cultured to create new plants.

In certain aspects, the invention relates to a method for identifying, detecting and/or selecting *Capsicum* plants producing or susceptible to produce fruits which are green at maturity and/or over-maturity and/or plants which can give rise to progeny plants producing or susceptible to produce fruits which are green at maturity and/or over-maturity, said method comprising the detection of a mutant allele of the cl gene and/or a mutant allele of the wt gene. In one embodiment, the method further comprises the detection of a mutant allele of the y gene. In particular, the method comprises the detection of mutant alleles as described in the present invention. In one aspect, the method comprises the detection of a specific marker in the cl gene, wherein the marker is associated with the C[T]T Indel between positions 174 and position 175 of the wild-type coding sequence of the cl gene, in particular in SEQ ID NO: 1. In another aspect, the method comprises the detection of a mutant allele of the cl gene by detecting the nucleic acid sequence set forth in SEQ ID NO: 9 or a complement thereof. More particularly, the method may use one or more nucleic acid primers or probes. In another aspect, the method comprises the detection of a mutant allele of the wt gene by detecting the presence or absence of a specific marker, e.g. a SCAR marker detected by PCR using the nucleic acid primers as set forth in SEQ ID NO: 10 and SEQ NO: 11.

In an additional aspect, the method involves determining the zygosity of the mutant allele, especially determining if said mutant allele is in homozygous form. Methods for detecting a specific nucleic acid marker are known in the art and may involve, for instance, the use of PCR primers or probes.

In certain aspects, the invention relates to an oligonucleotide primer or probe, wherein said oligonucleotide primer or probe is capable of detecting an allelic variation in the sequence of the cl, wt and/or y gene. In one embodiment, said oligonucleotide primer or probe is specific for a mutant allele of the cl gene, wherein said mutant allele comprises a C[T]T Indel between positions 174 and position 175 of the wild-type coding sequence of the cl gene, e.g. as set forth in SEQ ID NO: 1. In one aspect, said primer or probe is capable of detecting the sequence set forth in SEQ ID NO: 9 or a complement thereof.

In other aspects, the invention relates to a method for identifying, detecting and/or selecting *Capsicum* plants having a reduced susceptibility to blind phenotype, wherein said method comprises the detection of homozygous alleles at a QTL delimited by each of the markers set forth in SEQ ID NO: 7 or SEQ ID NO: 8 and/or delimited by positions 132028868 and 132040163 of the reference genome *Capsicum annuum* Pepper Zunla 1 Ref_v1.0. In one embodiment, said method comprises the detection of homozygous alleles of the sequences set forth in SEQ ID NO: 7 or SEQ ID NO: 8.

Preferably, said method involves the detection of at least one of the following alleles in homozygous form:

allele G or A of the sequence set forth in SEQ ID NO: 7 and/or allele G or A of the sequence set forth in SEQ ID NO: 8.

Detection of said alleles can be carried out according to various techniques available to the skilled person, e.g. by PCR amplification using primers, or by probes. A skilled person will understand that primers can be designed using the sequences disclosed in the present specification, in particular SEQ ID NO:7 and SEQ ID NO:8. Primers can also be designed using publically available pepper genome sequences, such as the reference genome *Capsicum annuum* Pepper Zunla 1 Ref_v1.0.

In one aspect, the invention relates to a method for identifying a molecular marker linked with a QTL associated with susceptibility to blind phenotype, comprising:

(a) identifying a molecular marker in the chromosomal region delimited on chromosome 8 by the nucleic acid sequences set forth in SEQ ID NO: 7 and SEQ ID NO: 8; and (b) determining whether an allele or state of said molecular marker is associated with susceptibility to blind phenotype in a segregating population comprising plants exhibiting the blind phenotype.

The molecular markers according to the present invention are preferably SNP markers.

According to another aspect, the present invention is directed to the use of a *Capsicum* plant of the invention as a breeding partner in a breeding program for obtaining *Capsicum* plants producing green mature fruits. Indeed, a *Capsicum* plant according to the invention harbors homozygously in its genome the mutant alleles for the cl and wt genes, conferring the phenotype of interest. By crossing this plant with another *Capsicum* plant, especially a line, it is thus possible to transfer the mutant alleles for the cl and wt genes to the progeny and, optionally the mutant alleles for the y gene. A plant according to the invention can thus be used as a breeding partner for introgressing the mutant alleles conferring the desired phenotype into a *Capsicum* plant or germplasm. For instance, the transfer of the mature and/or overmature green fruit phenotype (PermagreenWhite phenotype) of the plant of the invention into a different *Capsicum* plant can be used to develop new pepper varieties.

According to a particular aspect, the plant of the invention which can be used as a breeding partner can be grown from representative seed deposited at the NCIMB under accession number NCIMB 43123.

According to an aspect, the invention relates to a method for the production of a *Capsicum* plant producing fruits which are green at maturity and/or over-maturity, said method comprising:
  (a) Crossing a first *Capsicum* plant according to the invention, homozygously comprising mutant alleles of the cl and wt genes, with a second *Capsicum* plant, preferably a plant which does not produce fruits which are green at maturity and/or over-maturity;
  (b) self-pollinating the F1 *Capsicum* plants obtained at step (a);
  (c) selecting the F2 *Capsicum* plants obtained at step (b) which homozygously comprise a mutant allele in the cl gene and in the wt gene.

Steps (a) to (c) can be repeated one or more times, wherein the F2 *Capsicum* plants selected at step (c) can be used as new "first *Capsicum* plants" to be crossed with the second *Capsicum* plants in a new step (a). The second *Capsicum* plants can be always the same at each repetition. In such a case, the second *Capsicum* plant is the recurrent parent of an introgression breeding scheme, and the method of the invention can serve to introgress the Permagreen-White phenotype in a desired genetic background, for instance to develop new pepper varieties. Alternatively, different second *Capsicum* plants can be used at each repetition.

In one aspect, the method further comprises a step of selecting F2 *Capsicum* plants which homozygously comprise a mutant allele in the y gene.

In another aspect of the method, a marker-assisted selection is used at step (c) to identify the F2 *Capsicum* plants homozygously comprising a mutant allele of the cl gene and/or the wt gene, and/or the F2 *Capsicum* plants homozygously comprising a mutant allele of they gene.

In another aspect, the method comprises selecting F2 *Capsicum* plants which comprise homozygous alleles at a QTL in chromosome 8, wherein said QTL is delimited by each of the markers set forth in SEQ ID NO: 7 or SEQ ID NO: 8 and/or delimited by positions 132028868 and 132040163 of the reference genome *Capsicum annuum* Pepper Zunla 1 Ref_v1.0. In one embodiment, said method comprises selecting F2 *Capsicum* plants comprising homozygous alleles of the sequences set forth in SEQ ID NO: 7 or SEQ ID NO: 8.

In one aspect, the first *Capsicum* plant is a plant grown from a seed deposited at the NCIMB under accession number NCIMB 43123, or progeny thereof.

According to another aspect, the present invention relates to a method for growing *Capsicum* plants comprising sowing seeds according to the invention and growing the plants derived from said seeds. In one embodiment, less than 3%, preferably less than 1%, still preferably less than 1% of the grown plants have a blind phenotype. In one embodiment, more than 100 seeds, preferably more than 500 seeds are sown. In one embodiment, the *Capsicum* plant according to the invention is grown in an enclosure, in particular in a greenhouse or in a tunnel.

According to another aspect, the present invention relates to a method of producing pepper fruit comprising:
  a) growing a *Capsicum* plant according to the invention;
  b) allowing said plant to set fruit; and
  c) harvesting fruit of said plant.

Said fruit is preferably harvested at maturity or over-maturity, more preferably at maturity. Still preferably, when the fruit is harvested, it exhibits a green color which can be distinguished from the olive-green color of fruits of other plants, at the same stage of maturity, preferably wherein said other plants are existing permagreen peppers, still preferably wherein said other plants have a clclWTWT genotype, such as plants from the Evergreen or Sweet Green varieties.

The present invention also relates to a method of producing a food product, comprising mixing a pepper fruit of the invention, or part thereof, with one or more food ingredients. Optionally, the method comprises cooking and/or processing the pepper fruit of the invention, alone or in mixture with the one or more food ingredients. Examples of food products that comprise pepper in raw, cooked or otherwise processed form include powders, soups, sauces, salsas, pastas, condiments, pastries, sweets and salads. Preferably, the pepper fruit of the invention, as used and/or comprised in food products, keeps its color difference with fruits having a clclWTWT genotype as used in similar conditions.

The present invention also relates to a food product made of a pepper fruit of the invention or parts thereof, optionally in processed form.

In another aspect, the invention relates to the use of a *Capsicum* plant according to the invention or a fruit thereof in the fresh cut market or for food processing. Techniques for using pepper in food processing are well known from the skilled person, e.g. as an ingredient in a food product such as powders, soups, sauces, salsas, pastas, condiments, pastries, sweets and salads, and described, for instance, in Handbook of Food Science, Technology and Engineering, vol. 4, Y. H. Hui, Frank Sherkat. CRC Press. Pepper fruit color is an important purchase criterion, in particular in the fresh cut market, and the green color at maturity and/or over-maturity of fruits of the invention offers a competitive advantage by distinguishing these fruits over existing varieties, in particular existing permagreen varieties producing olive-green fruits.

In a further aspect, the invention also concerns a method for improving the marketability of green pepper fruit, wherein said method comprises growing *Capsicum* plants according to the invention and harvesting fruits set by said plants.

The present invention will be further illustrated by the following examples, which should not be construed as limiting in any way.

Seed Deposit

A representative sample of seeds from the *Capsicum annuum* plant according to the invention (i.e. seeds from PGR1 plant) has been deposited by Vilmorin S. A., Route du Manoir, 49250 La Ménitré, France, pursuant to, and in satisfaction of, the requirements of the Budapest Treaty on the International Recognition of the Deposit of Microorganisms for the Purposes of Patent Procedure (the "Budapest Treaty") with the National Collection of Industrial, Food and Marine Bacteria (NCIMB), Ferguson Building, Craibstone Estate, Bucksburn, Aberdeen, Scotland, AB21 9YA, United Kingdom, on Jul. 26, 2018, under accession number 43123.

A deposit of the PGR1 seeds is maintained by Vilmorin S. A., Route du Manoir, 49250 La Ménitré, France.

Example 1

Identification of a New cl Mutant and Development of a Marker

The bell pepper accession PM1137 is a permagreen line which produces fruits having an olive-green color at maturity and over-maturity. PM1137 is homozygous recessive for the two genes cl and y responsible for the color of pepper fruits at maturity. The cl gene of PM1137, and several other *Capsicum* genotypes (including Sweet Green, Evergreen, Yolo Wonder and PI159234) was sequenced from amplified DNA fragments. The sequences were aligned together and with reference sequences from NCBI Genbank, including EU196733 (update Jul. 14, 2008, SEQ ID NO: 14) and EU414631 (update Apr. 29, 2008, SEQ ID NO: 15). A SNP was detected for PM1137, within the second exon of the cl gene, between positions 174 and 175 of the cDNA, corresponding to an Indel C[T]T with respect to the wild-type sequence. A nucleic acid marker "CL_3" was developed (sequence: TTTGGGAGTTGATGAGAAAAAGCACC (SEQ ID NO: 13), wherein the first thymine corresponds to the inserted thymine in the mutant allele), corresponding to this polymorphism. By way of contrast, the dCAPS marker corresponding to the mutation [T/C] at nucleotide 340 as described in Borovsky and Paran, Theor Appl Genet (2008) 117:235-240, was not detected in PM1137. The inventors tested several pepper lines for the presence of the CL_3 marker, including known "permagreen" varieties Evergreen and Sweet Green.

TABLE 1 analysis of several pepper lines for the presence of the CL_3 marker

| Line | Mature fruit color | Call | CL_3 | InDel |
| --- | --- | --- | --- | --- |
| PM1137 = permagreen bell | olive-green | X:X | Yes | C[T]T |
| Evergreen | olive-green | Y:Y | No | C[ ]T |
| Sweet Green | olive-green | Y:Y | No | C[ ]T |
| Internal control | olive-green | Y:Y | No | C[ ]T |
| PI 159234 | not green | Y:Y | No | C[ ]T |
| Yolo Wonder | not green | Y:Y | no | C[ ]T |

The C[T]T InDel is a null mutation, which introduces a frameshift in the cl gene, wherein said frameshift stops translation, such that the CaSGR protein is synthesized in a truncated form. This mutation therefore differs in its effect compared to the [T/C] mutation in position 340 described by Borovsky and Paran (see infra) which, according to the authors, induces an amino-acid substitution in CaSGR. The authors hypothesize that this substitution causes a partial and not full inhibition of chlorophyll degradation and, as a consequence, in a yellowing of the pepper fruits at over-maturity.

Example 2

Generation of a PermagreenWhite (PGW) Pepper Plant

In order to improve the color of permagreen peppers at fruit maturity and over-maturity, the present inventors crossed a permagreen plant with a permawhite plant. The permagreen parent was a F4 BC2 from the Permagreen bell pepper PM1137, genetically clclWTWT, with fruits turning olive-green at maturity and over-maturity. The permawhite parent was a plant from accession PI640876, genetically ClClwtwt, with fruits turning from white at maturity to ivory at over-maturity.

The F1 hybrids obtained from the crossing of the permagreen and permawhite parents were selfed and a F2 population was obtained. The F2 plants were tested for the presence of the CL_3 marker and for a SCAR marker of the wt gene, amplified using the primers set forth in SEQ ID NO: 10 (forward primer: GAGGGTCACCAGTGATACG) and SEQ ID NO: 11 (reverse primer GCCTGTGCTAATT-CATCTTGAGGC). A wild type wt allele yields a 1207 bp (gDNA) or 351 bp (cDNA) fragment, while there is no amplified fragment for a mutant wt allele.

TABLE 2 segregation of the markers for the cl and wt genes in a F2 population

| Expected mature fruit color | Cl genotype | Wt genotype | Number of plants | % of total | % expected |
| --- | --- | --- | --- | --- | --- |
| Light yellow to orange-yellow | CL/CL or CL/cl | wt/WT or WT/WT | 245 | 57% | 56% |
| cream | CL/CL or CL/cl | wt/wt | 80 | 19% | 19% |
| olive green | cl/cl | wt/WT or WT/WT | 80 | 19% | 19% |
| green | cl/cl | wt/wt | 22 | 6% | 6% |

The segregation pattern is as expected for two recessive genes.

In the F2 populations, a high proportion of blind plants was observed (from 7% to 36%).

Example 3

Color Measurement Protocol

The color of pepper fruits was measured and analyzed as follows.

Once harvested, fruits were cleaned up to remove any traces of earth, stain or droplet of water. The peduncles of the fruits were removed in order to avoid any interference by the green color of the peduncle, and measure only the color of the fruit.

Pictures were taken by a high resolution camera (IDS uEye camera, with USB connection and a fixed lens of 10 MPix), in a closed space (83*83*83 cm), homogenously illuminated with controlled artificial light (5000K LED). The fruits were placed in front of a uniformly black background in order to obtain standardized pictures. The software and driver used to control the camera were the standard ones provided with the camera.

Reference objects were positioned at fixed positions on the black background. These objects were a 10 euro cent coin (useful to assess the shape of cup-shaped fruits), a QpCard 201 (color reference), 2 graduated rulers and a tag with the code of the analyzed fruits.

The camera's focus (aperture and sharpness) was set using the QpCard. In order to validate the camera settings, a picture was generated in an uncompressed BMP format, and was analyzed using the Image J software. The settings were considered to be correct if the light blue and light green patches of the QpCard were visible on the screen and if the 4 grey patches in the 4 corners of the QpCard had R,G,B values close to 180. Otherwise, the camera's settings had to be adjusted until these criteria are met.

Once the settings were correct, a picture was taken containing the whole fruits to be analyzed, their separated peduncles, and the reference objects. The peduncles were positioned at the top of the area to be photographed. The fruits were placed below the peduncles, and were positioned and spaced apart from one another in such a way as to avoid any projected shadows (a projected shadow would make 2 adjacent fruits be considered as a single fruit).

The pictures were then converted into raw RGB data. For each fruit, up to 3000 random pixels/fruit are analyzed and converted into RGB data. The mean R, mean G and mean B values per fruit were then calculated for all analyzed fruits and all images, as well as the 3 ratios mean R/mean G, mean R/mean B and mean G/mean B.

Color Analysis of Mature Fruits from Various Lines Grown in Tunnel

Different populations of pepper plants were grown in a tunnel and their fruits were harvested at the same stage of maturity, namely fully developed mature fruits with an optimal firmness. 452 fruits were selected and their color was analyzed according to the colorimetry protocol described herein. This comprises 308 fruits visually appearing olive-green and genetically clclWTWT (83 F2 Sweet Green fruits, 163 permagreen parent (F4 PG) fruits and 62 permagreen PM1137 fruits) and 144 PermagreenWhite fruits (genetically clclwtwt), of a dihaploid line obtained as described in the present disclosure, said PermagreenWhite fruits visually appearing green.

The mean R, mean G and mean B values were obtained for each fruit, as well as the ratios mean R/mean G, mean G/mean B and mean R/mean B, as described above. FIGS. 1 to 6 show these parameters for the 4 analyzed pepper populations.

Figure 5:
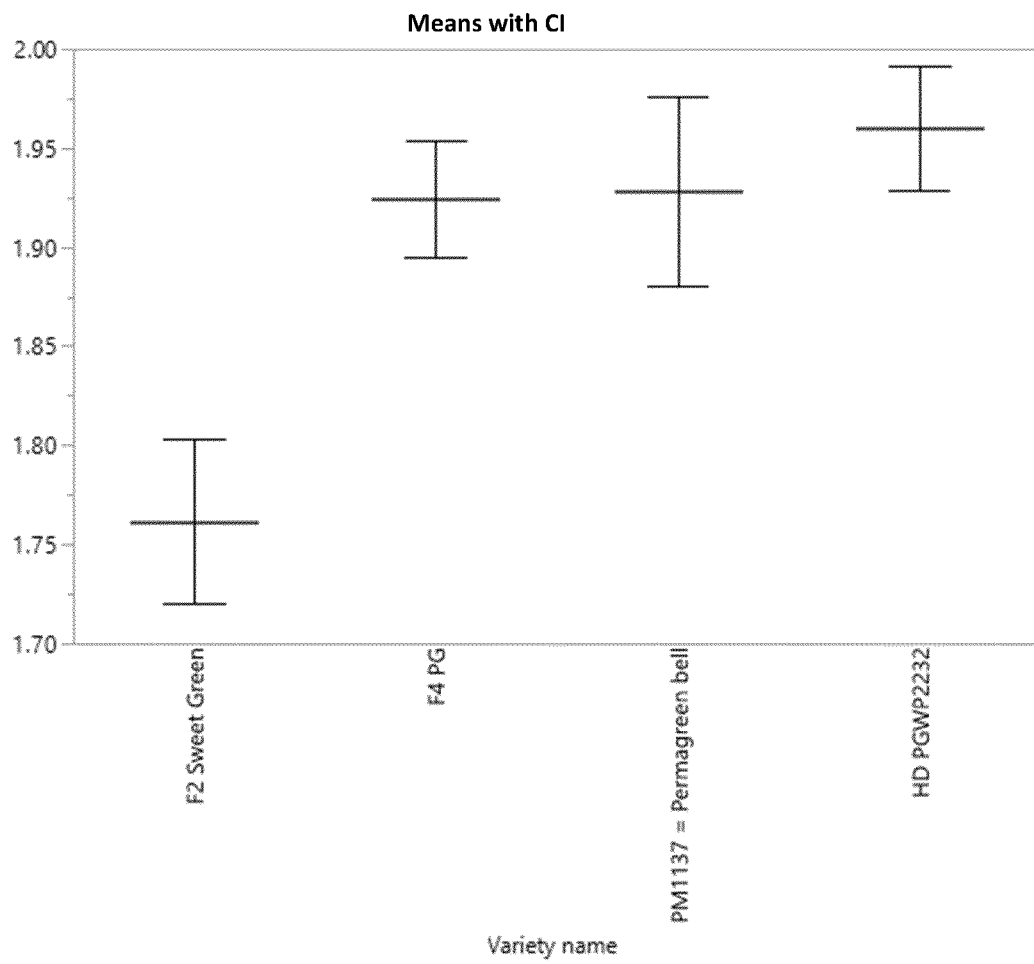
FIG. 5: Panel A shows the mean R/mean B (red/blue) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.
Figure 6:
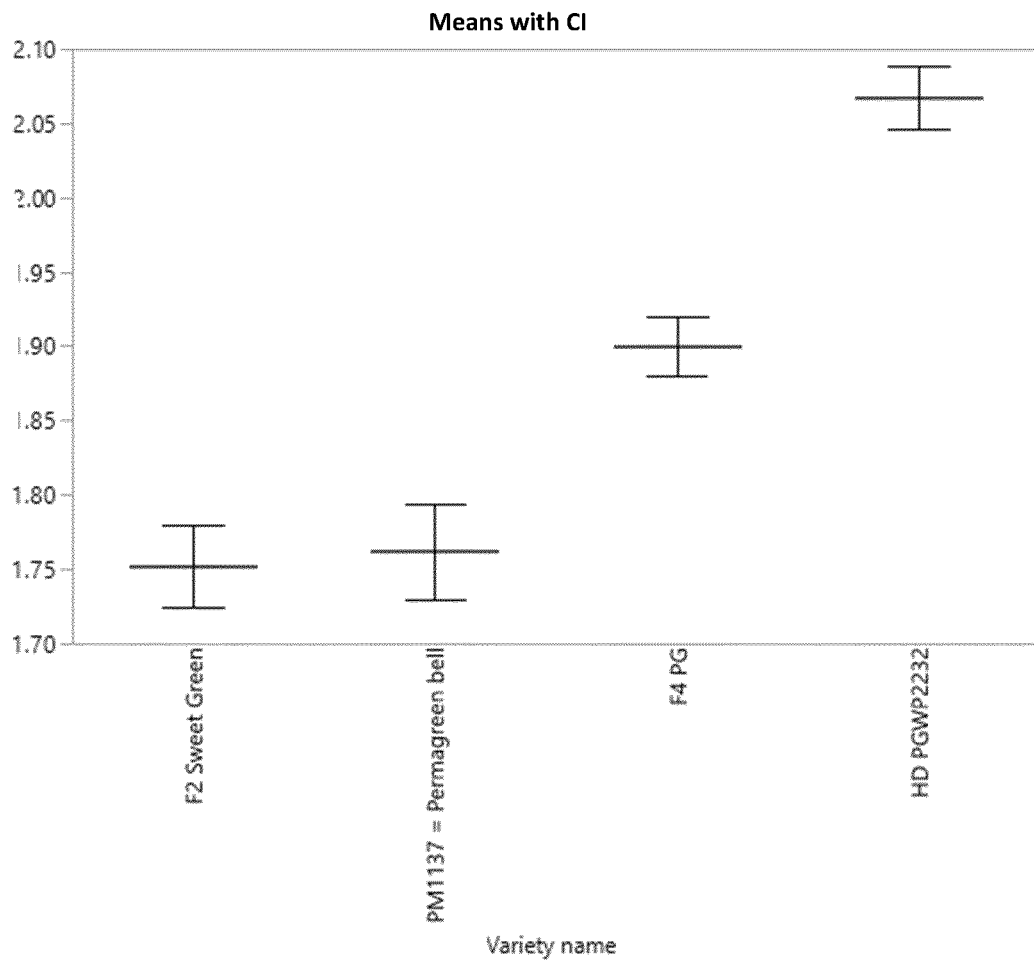
FIG. 6: Panel A shows the mean G/mean B (green/blue) value measured on fruits of PermagreenWhite plants according to the invention (HD PGWP2232), fruits of the permagreen parent (F4 PG), fruits of accession PM1137 (PM1137=Permagreen bell) and fruits of F2 Sweet Green plants. Panel B shows the results of a post-hoc Tukey's HSD test.

A one-way ANOVA with post-hoc Tukey's HSD, test reveals significant differences ($p<0.05$) between the color of the PermagreenWhite fruits and the color of each of the three olive-green populations (F2 Sweet Green, F4 PG and PM1137), for all three mean R, mean G and mean B variables as well as for the mean R/mean G and mean G/mean B ratios (FIGS. 1 to 4 and 6). The mean R/mean B ratio is also significantly different between the Permagreen-White fruits and the F2 Sweet Green fruits (FIG. 5).

The different fruit populations were also compared using a one-way ANOVA with post-hoc Dunnett's test, using the F2 Sweet Green as control. The Dunnett's test confirms that the PermagreenWhite fruits are significantly different from the F2 Sweet Green fruits, for all 6 variables tested (R, G, B, mean R/mean G, mean G/mean B and mean R/mean B).

These results confirmed the visual observation of the fruits, which already shown a clear difference between the green color of PermagreenWhite mature fruits and the olive-green color of the existing permagreen lines, such as Sweet Green, or PM1137. Similar results are expected for colorimetric comparisons between PermagreenWhite fruits according to the invention and fruits of any plant having the same genotype as Sweet Green at the cl, wt and y loci.

Example 4

Genotyping and Generation of a Genetic Map

Several plant populations were genotyped using an Affymetrix chip: the permawhite parent (PI640876), the permagreen parent (F4 PG) (2 plants per parent), the permagreen bell pepper PM1137 (2 plants) and 4 plants from a F2 Sweet Green as well as 356 plants from the segregating F2 population resulting from the crossing between the permagreen parent and the permawhite parent (F2 PGxPW). The Affymetrix chip comprised 7000 SNPs distributed over the 12 chromosomes of pepper genome.

The genotyping results of the permagreen (F4 PG) and permawhite parents as well as of PM1137 and F2 Sweet Green, were analyzed and the SNPs with missing data as well as the monomorphic markers were discarded, resulting in a matrix of 5782 polymorphic SNPs. The CallRate was higher than 96% for all genotyped plants, and the Heterozygosity Rate was very low for the permawhite and PM1137 plants (0.11%) and slightly higher for the F4 PG population (1.46%) and the F2 Sweet Green (7.01%), which populations have slight tendency to segregate.

The initial matrix comprising 5782 SNPs was filtered using the data obtained with the 356 F2 PGxPW plants. 3578 SNPs monomorphic for this F2, as well as 176 SNPs with a CallRate lower than 80%, were filtered out of the matrix, resulting into a matrix comprising 2028 SNPs and 356 F2 PGxPW plants. A consensus genotype was then generated for the two parents (permagreen (F4 PG) and permawhite) by comparing the two genotyped plants of each parent: the SNPs which have a different call between the two plants of a parent were discarded, as well as those with a missing call.

A new matrix was generated, comprising 1883 SNPs and 358 plants (356 F2 PermagreenWhite plants, one consensus parent permawhite plant and one consensus parent permagreen plant). This matrix in format "ATGC" was converted into a matrix in format "ABH", where, for each SNP, "A" means homozygous for the permawhite allele, "B" means homozygous for the permagreen allele and "H" means heterozygous. 1711 SNPs were converted, whilst the SNPs with a missing call ("NA") were discarded as well as the SNPs heterozygous for one of the parents. The genetic map was built using the JoinMap 4 software (Van Ooijen, J. W., 2006. JoinMap® 4 Software for calculation of genetic linkage maps in experimental populations. Kyazma B. V., Wegeningen, Netherlands). A $\chi^2$ test was then carried out for each SNP, in order to assess whether the segregation of each SNP across the F2 PermagreenWhite population, is conform to that theoretically expected for a F2 population and a dominant gene (3:1 ratio). 38 SNPs having a significant $\chi^2$ (threshold 0.0001) were excluded from the analysis: 3 SNPs with too many missing data, 8 SNPs with no "H", 2 SNPs with no "B" and 25 SNPs with no "A".

The SNPs were then grouped in twelve linkage groups based on a test of independence (LOD score).

A genetic map was then generated: the link between each locus within a same group was calculated pairwise. The order of the markers within each group and their mutual distance was then established using maximum likelihood mapping and a conversion to genetic distances using the Kosambi's mapping function. The linkage groups were then translated into chromosomes, using the Pepper Zunla-1 Ref_v1.0 reference genome (Qin, Cheng, et al. "Whole-genome sequencing of cultivated and wild peppers provides insights into *Capsicum* domestication and specialization." *Proceedings of the National Academy of Sciences* 111.14 (2014): 5135-5140).

Observation and Rating of Blind Plants

The inventors found out that the PermagreenWhite plants comprised a significant proportion of plants with a blind phenotype, in particular in the F2 or F3 populations. The parent permagreen line (F4 PG) and permawhite line (PI640876) do not exhibit this phenotype. In order to identify potential genetic causes for this phenotype in the hybrids, the inventors carried out a QTL mapping of the blind phenotype.

The inventors first rated a F2 population of Permagreen-White plants for the presence of a blind phenotype or similar phenotypes such as "abnormal" or "chimeric" plants. To this effect, F2 PermagreenWhite seeds were sown in mini-clods or starter trays. The plantlets were observed early April, at the 1-leaf stage and were again observed three days before their transplantation in tunnels. The plantlets were rated according to a binary rating system, where "1" corresponds to normal plantlets and "2" corresponds to blind, chimeric and abnormal plantlets (variable "blind, plantlet stage").

Figure 7:
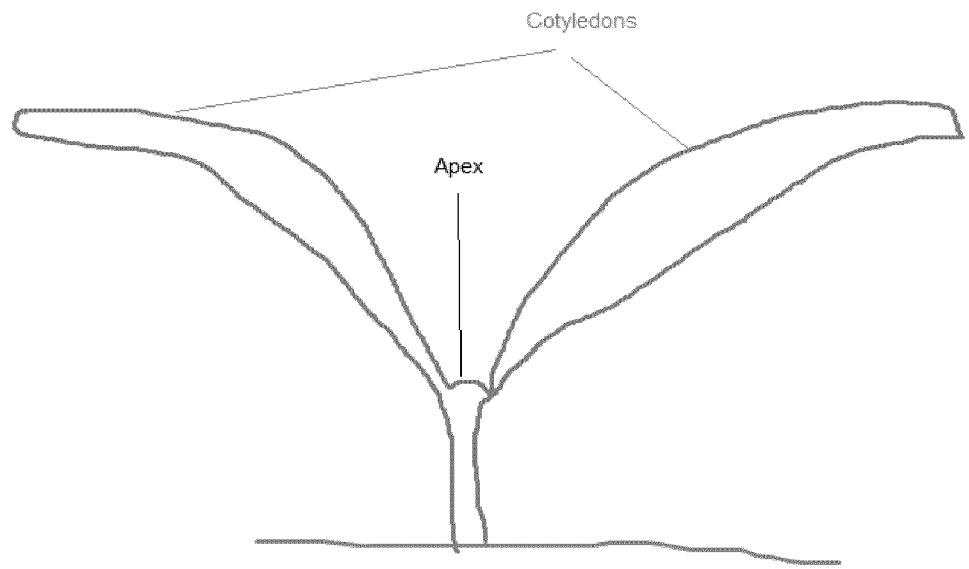
FIG. 7 is a schematic drawing of a blind plantlet having its two cotyledons and no development of an apex
Figure 8:
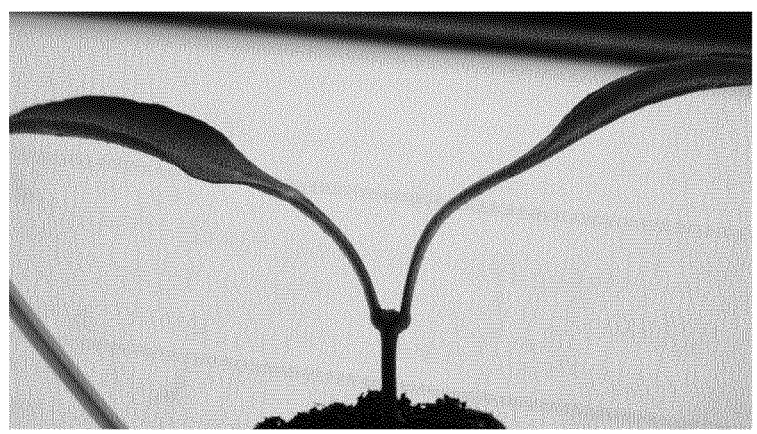
FIG. 8 is a photograph of a blind plantlet having its two cotyledons and no development of an apex
Figure 9:
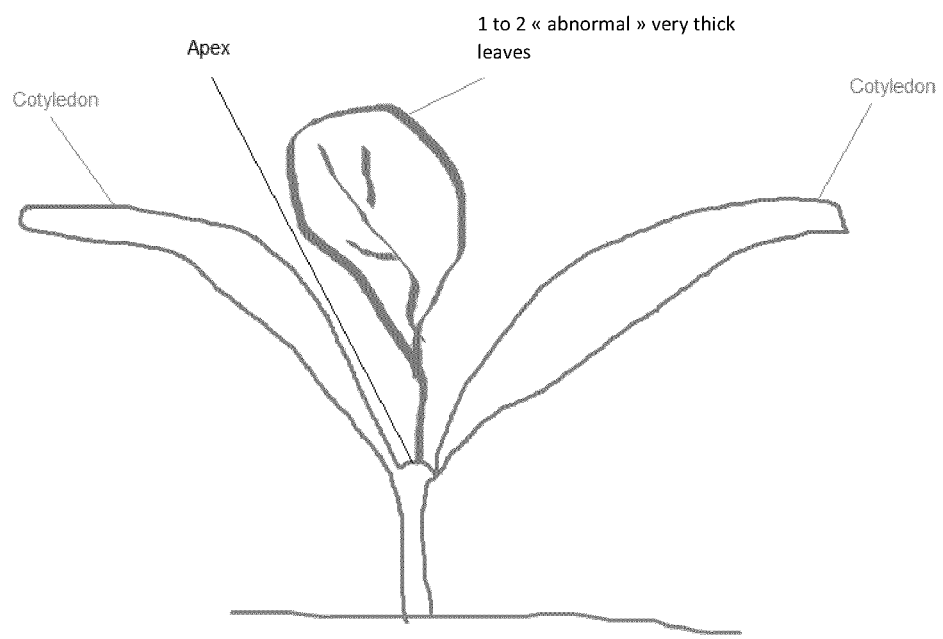
FIG. 9 is a schematic drawing of a blind plantlet which has only one or two leaves growing from the apex, the leaf or leaves being much thicker than normal leaves and having an abnormal shape.
Figure 10:
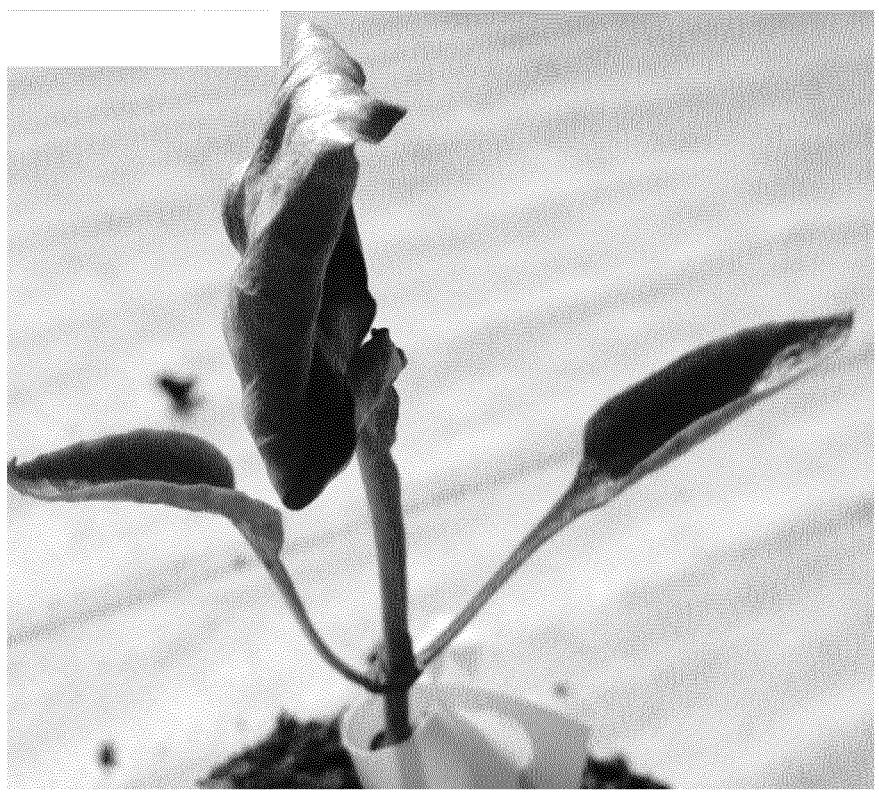
FIG. 10 is a photograph of a blind plantlet which has only one or two leaves growing from the apex, the leaf or leaves being much thicker than normal leaves and having an abnormal shape.
Figure 11:
FIG. 11 is a photograph of an abnormal plantlet comprising several stems and apexes.
Figure 12:
FIG. 12 is a photograph of an abnormal plantlet comprising several stems growing from the plant collar (an enlargement is shown in the top right panel).

A plantlet was rated blind ("2") when the plantlet has its 2 cotyledons without apex (FIGS. 7 and 8) or when the plantlet had only one or two leaves growing from the apex, the leaf or leaves being much thicker than normal leaves and/or their shape being abnormal (FIGS. 9 and 10). In order to encompass a broad scope of architectural and morphological defects, a number of plantlets were rated "2" although they did not exhibit a blind phenotype in the strict meaning of the term, but presented other types of morphological and architectural defects: these plants are called abnormal or chimeric. Abnormal or chimeric plantlets are for instance plantlets with several stems and several apexes, plantlets with several stems starting from a single apex, plantlets with a well-developed apex and main stem, but with only few leaves present on the stem (with a long internode distance) or plantlets with an apex present on a secondary stem. Examples of abnormal or chimeric plantlets are shown in FIGS. 11 and 12.

The plants were then allowed to grow and observed again at the harvest stage in July, i.e. when mature fruits could be harvested from the pepper plants and, when necessary, analyzed for their color. At the harvest stage, the adult plants were again rated according to a binary rating system, where "1" corresponds to normal adult plants and "2" corresponds to blind, chimeric and abnormal plants (variable "blind, harvest stage").

QTL Detection by Interval Mapping

QTL interval mapping was carried out using the MapQTL 5 Software (Van Ooijen, J. W., 2004. MapQTL*5 Software for the mapping of quantitative trait loci in experimental populations. Kyazma B. V., Wageningen, Netherlands, based on the genetic map built as described above.

A F2 Permagreen×Permawhite (PG×PW) population was rated for the presence of the blind phenotype (including abnormal and chimeric plants), as described above.

A QTL search was performed using Interval Mapping method for the variable "Blind, chimeric and abnormal plantlets", as described above.

The probability for the presence of a QTL was calculated every cM on the genome, as well as the effect of the QTL and the residual variance. The probabilities for the presence of a QTL for H0 (null hypothesis: absence of a QTL) and H1 (alternative hypothesis: presence of a QTL) were then compared. A permutation test was applied to each data set to determine the LOD (Logarithm of odds) thresholds. A genome-wide LOD threshold of 3.0 was used for QTL significance (p<0.05). The chromosomal locations with the highest LOD scores (LOD peak) were considered to be the most likely positions of a QTL. The QTL interval, corresponding to the chromosomal portion with a LOD>3.0, was translated into a physical interval by projecting markers onto the Pepper Zunla-1 Ref_v1.0 reference genome.

Figure 13:
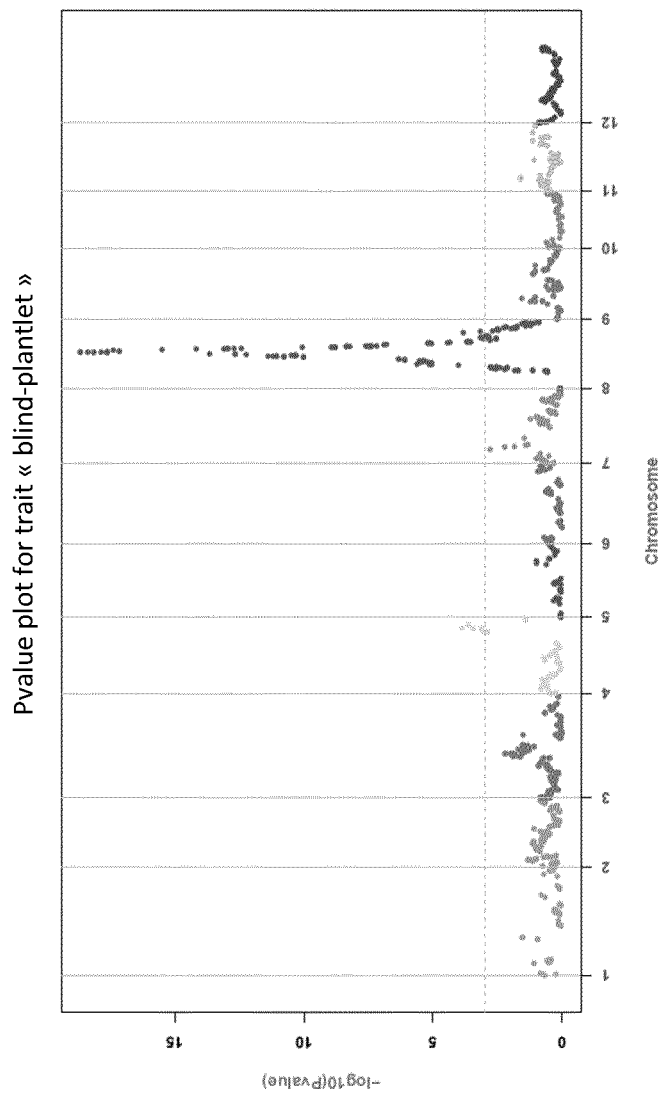
FIG. 13 represents the logarithm of odds (LOD), across the whole pepper genome, for the blind phenotype at plantlet stage.

A QTL was mapped on chromosome 8 for the variable "blind, plantlet stage". The effect of this QTL explains 22% of the phenotypic variation. This QTL was confirmed when the tested variable was "blind, harvest stage". FIG. 13 shows the likelihood profile of QTL mapping, as physically mapped on chromosomes 1 to 12 of the Pepper Zunla-1 Ref_v1.0 reference genome.

The position of the QTL on chromosome 8, its likelihood (LOD) and its effect on the phenotypic variance ($R^2$ values), are shown in Table 3, as well as the genotypes of the permawhite and permagreen parents at two SNPs linked with said QTL.

TABLE 3 list of SNPs with the highest LOD for the variable "blind, plantlet stage", their position and the alleles found in the F4 permagreen parent (PG allele) and in the permawhite parent (PW allele).

| Chromosome | Position in the Pepper Zunla 1 Ref_v1.0 reference genome | LOD | $R^2$ | Permawhite genotype ("A") | Permagreen genotype ("B") | Genotype of PGW plants comprising the QTL in heterozygous form ("H") |
|---|---|---|---|---|---|---|
| 8 | 132028868 | 18.79 | 21.6 | G/G | A/A | G/A |
| 8 | 132040163 | 18.79 | 21.6 | G/G | A/A | G/A |

An analysis of the allelic effect shows that both parental alleles have a positive effect on the absence of blind phenotype, when these alleles are present in the homozygous state ("A" or "B"), the effect of the permawhite allele being slightly more positive than that of the permagreen allele. When the alleles are present in the heterozygous state ("H"), they have a negative effect on the blind phenotype.

A pseudo-linkage between chromosomes P1 and P8 has been reported in *Capsicum* populations (Wu et al., Theor Appl Genet (2009), 118(1279-1293); Hill et al., G3 (Bethesda) (2015), 5(11):2341-2355). This pseudo-linkage could explain the linkage drag between the blind phenotype, having a responsible QTL on chromosome 8, and the genetic determinants of the PermagreenWhite phenotype, in particular the cl gene which is located on chromosome 1.

An alternative QTL mapping was carried out using a continuous rating scale, from 1 (normal plant) to 5 (no development or weak development of chimeric leaves), at the plantlet stage. A QTL for the blind phenotype was identified at the same position as described above for the QTL mapping using a binary scale. This confirms the robustness of the QTL identification.

Although the invention has been described and illustrated in the foregoing illustrative embodiments it is understood that the present disclosure has been made only by way of example, and that numerous changes in the details of implementation of the invention can be made without departing from the spirit and scope of the invention, which is only limited by the claims which follow. In particular, features of the disclosed embodiments can be omitted, combined and rearranged in various ways.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

LIST OF REFERENCES CITED IN THE DESCRIPTION

Borovsky and Paran, Theor Appl Genet (2008), 117:235-240
Comai et al., Plant J (2004), 37: 778-86 de Jonge, J., Goffman, F. D., Kodde, J., Angenent, G. C., & Groot, S. P. (2018). *Scientia Horticulturae,* 228, 76-80.

Gao et al., Nature Biotechnology (2016), 34: 768-773

Hurtado-Hernandez, H., & Smith, P. G., Journal of Heredity (1985), 76(3): 211-213

Kang, H. S., Kim, S. H., Lee, S. W. et al., Hortic. Environ. Biotechnol. (2018), 59: 447

Kim, Ok Rye, et al., Molecules and cells (2010), 30(6): 569-574

Lefebvre, Véronique, et al. Plant molecular biology (1998), 36(5): 785-789

LeKim, Jeong Eun, et al., Horticultural Science and Technology (2017), 35(5): 599-607

Till B J, Zerr T, Comai L, Henikoff S., Nat Protoc (2006), 1(5): 2465-77

Qin, Cheng, et al., Proceedings of the National Academy of Sciences (2014), 111(14): 5135-5140

Thorup, T. A., et al. Proceedings of the National Academy of Sciences (2000), 97(21): 11192-11197

Van Ooijen, J. W., 2004. JoinMap® 4 Software for calculation of genetic linkage maps in experimental populations. Kyazma B. V., Wegeningen, Netherlands Van Ooijen, J. W., 2004. MapQTL*5 Software for the mapping of quantitative trait loci in experimental populations. Kyazma B. V., Wageningen, Netherlands Wetzstein, Hazel Y., and Charles S. Vavrina. "Morphological evaluation of apical meristem decline in greenhouse-grown tomato transplants and the effect of mineral nutrition on its occurrence." *Journal of the American Society for Horticultural Science* 127.4 (2002): 635-638.

Wu et al., Theor Appl Genet (2009), 118(1279-1293)

The invention claimed is:

1. A *Capsicum* plant or a plant part or cell thereof, wherein said plant, plant part or cell homozygously comprises in its genome:
   (a) a loss-of-function mutant allele of the cl gene encoding a *Capsicum* stay-green (CaSGR) protein, wherein a wild-type sequence of the cl gene is set forth in SEQ ID NO:1, and
   (b) a loss-of-function mutant allele of the wt gene encoding a phytoene synthase (PSY) protein, wherein a wild-type sequence of the wt gene is set forth in SEQ ID NO:3.

2. The *Capsicum* plant, plant part or cell according to claim 1, wherein said plant, plant part or cell homozygously further comprises in its genome a loss-of-function mutant allele of the y gene encoding a capsanthin-capsorubin synthase (CCS) protein, wherein a wild-type sequence of the y gene is set forth in SEQ ID NO:5.

3. The *Capsicum* plant, plant part or cell according to claim 1, wherein said mutant allele of the cl gene is a null allele.

4. The *Capsicum* plant, plant part or cell according to claim 2, wherein said mutant alleles of the cl, wt and/or y genes are present in representative seeds deposited at NCIMB under accession number 43123.

5. The *Capsicum* plant, plant part or cell according to claim 1, wherein said plant is a *Capsicum annuum*, *Capsicum baccatum*, *Capsicum frutescens*, *Capsicum chinense*, *Capsicum pubescens* or *Capsicum chacoense* plant.

6. The *Capsicum* plant, plant part or cell according to claim 1, wherein said plant, plant part or cell is obtained by breeding with a plant grown from a seed deposited at NCIMB under accession number 43123.

7. The *Capsicum* plant part according to claim 1, wherein the plant part is a seed, explant, reproductive material, scion, cutting, fruit, root, rootstock, pollen, ovule, embryo, protoplast, leaf, anther, stem, petiole or flower.

8. The *Capsicum* cell according to claim 1, wherein the cell is obtained from an embryo, protoplast, meristematic cell, callus, pollen, leaves, anther, stem, petiole, root, root tip, fruit, seed, flower, cotyledon, and/or hypocotyl.

9. A *Capsicum* seed, which can be grown into the *Capsicum* plant according to claim 1.

* * * * *